United States Patent
Smith et al.

(10) Patent No.: US 11,254,970 B2
(45) Date of Patent: *Feb. 22, 2022

(54) DETECTING NUCLEIC ACID

(71) Applicant: Cascade Biosystems, Inc., Colfax, WI (US)

(72) Inventors: Kenneth D. Smith, Colfax, WI (US); Nina Yazvenko, Vancouver, WA (US); Mariya Smit, Vancouver, WA (US)

(73) Assignee: Cascade Biosystems, Inc., Colfax, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/846,663

(22) Filed: Apr. 13, 2020

(65) Prior Publication Data

US 2020/0248242 A1    Aug. 6, 2020

Related U.S. Application Data

(63) Continuation of application No. 15/587,944, filed on May 5, 2017, now Pat. No. 10,619,193, which is a (Continued)

(51) Int. Cl.
*C12Q 1/6823* (2018.01)
*C12Q 1/682* (2018.01)
(Continued)

(52) U.S. Cl.
CPC ............ *C12Q 1/6823* (2013.01); *C12Q 1/682* (2013.01); *C12Q 1/683* (2013.01); *C12Q 1/6806* (2013.01); *C12Q 1/6825* (2013.01); *C12Q 1/6834* (2013.01); *C12Q 1/6897* (2013.01)

(58) Field of Classification Search
CPC ....... C12Q 1/6823; C12Q 1/682; C12Q 1/683
See application file for complete search history.

(56) References Cited

U.S. PATENT DOCUMENTS

| 4,699,876 A | 10/1987 | Libeskind |
|---|---|---|
| 4,775,619 A | 10/1988 | Urdea |

(Continued)

FOREIGN PATENT DOCUMENTS

| WO | WO 1998/004738 | 2/1998 |
|---|---|---|
| WO | WO 1998/004739 | 2/1998 |

(Continued)

OTHER PUBLICATIONS

Albretsen et al., "Applications of magnetic beads with covalently attached oligonucleotides in hybridization: isolation and detection of specific measles virus mRNA from a crude cell lysate," Anal. Biochem., 1990, 189(1):40-50.

(Continued)

*Primary Examiner* — Samuel C Woolwine
(74) *Attorney, Agent, or Firm* — Fish & Richardson P.C.

(57) ABSTRACT

This document provides methods and materials for detecting target nucleic acid. For example, methods and materials for detecting the presence or absence of target nucleic acid, methods and materials for detecting the amount of target nucleic acid present within a sample, kits for detecting the presence or absence of target nucleic acid, kits for detecting the amount of target nucleic acid present within a sample, and methods for making such kits are provided.

11 Claims, 10 Drawing Sheets

Specification includes a Sequence Listing.

Related U.S. Application Data continuation of application No. 14/487,978, filed on Sep. 16, 2014, now Pat. No. 9,677,120, which is a continuation of application No. 14/135,121, filed on Dec. 19, 2013, now Pat. No. 8,865,407, which is a continuation of application No. 13/603,257, filed on Sep. 4, 2012, now Pat. No. 8,632,974, which is a continuation of application No. 12/535,017, filed on Aug. 4, 2009, now Pat. No. 8,278,048.

(60) Provisional application No. 61/166,843, filed on Apr. 6, 2009, provisional application No. 61/089,392, filed on Aug. 15, 2008.

(51) Int. Cl.
| | |
|---|---|
| C12Q 1/683 | (2018.01) |
| C12Q 1/6834 | (2018.01) |
| C12Q 1/6806 | (2018.01) |
| C12Q 1/6825 | (2018.01) |
| C12Q 1/6897 | (2018.01) |

(56) References Cited

U.S. PATENT DOCUMENTS

| | | |
|---|---|---|
| 5,102,784 A | 4/1992 | George, Jr. |
| 5,403,711 A | 4/1995 | Walder et al. |
| 5,679,510 A | 10/1997 | Ray et al. |
| 5,795,718 A | 8/1998 | Eisenbeis |
| 5,858,665 A | 1/1999 | Hepp et al. |
| 6,110,677 A | 8/2000 | Western et al. |
| 6,114,117 A | 9/2000 | Hepp et al. |
| 6,156,953 A | 12/2000 | Preuss et al. |
| 6,492,120 B1 | 12/2002 | Galvan et al. |
| 6,825,010 B2 | 11/2004 | Spier et al. |
| 7,524,629 B2 | 4/2009 | Olek et al. |
| 8,470,533 B2 | 6/2013 | Smith et al. |
| 8,551,701 B2 | 10/2013 | Smith et al. |
| 8,597,886 B2 | 12/2013 | Smith et al. |
| 8,623,616 B2 | 1/2014 | Smith et al. |
| 9,150,921 B2 | 10/2015 | Smith et al. |
| 9,150,932 B2 | 10/2015 | Smith et al. |
| 9,150,935 B2 | 10/2015 | Smith et al. |
| 9,399,802 B2 | 7/2016 | Smith et al. |
| 9,428,814 B2 | 8/2016 | Smith et al. |
| 9,689,037 B2 | 6/2017 | Smith et al. |
| 2002/0015951 A1 | 2/2002 | Bader et al. |
| 2002/0123620 A1 | 9/2002 | Danenberg |
| 2003/0124594 A1 | 7/2003 | Church et al. |
| 2003/0235837 A1 | 12/2003 | Keim et al. |
| 2004/0023207 A1 | 2/2004 | Polansky |
| 2005/0003390 A1 | 1/2005 | Axenovich et al. |
| 2006/0172325 A1 | 8/2006 | Brownstein et al. |
| 2006/0240431 A1 | 10/2006 | Fu |
| 2007/0161016 A1 | 7/2007 | Afar et al. |
| 2007/0231800 A1 | 10/2007 | Roberts et al. |
| 2008/0021205 A1 | 1/2008 | Blau et al. |
| 2009/0263809 A1 | 10/2009 | Roberton et al. |

FOREIGN PATENT DOCUMENTS

| | | |
|---|---|---|
| WO | WO 1998/019168 | 5/1998 |
| WO | WO 2002/059359 | 8/2002 |
| WO | WO 2004/101788 | 11/2004 |
| WO | WO 2004/108897 | 12/2004 |
| WO | WO 2010/019414 | 2/2010 |

OTHER PUBLICATIONS

Beaucage et al., "Deoxynucleoside phosphoramidites—a new class of key intermediates for deoxypolynucleotide synthesis," Tet. Let., 1981, 22(20):1859-1862.

Bekkaoui et al., "Cycling probe technology with RNase H attached to an oligonucleotide," BioTechniques, Feb. 1996, 20:240-248.

Black, Microbiology. Principles and Applications, Third Edition, 1996, pp. 144-148.

Chan et al., "Quantitative Analysis of Circulating Methylated DNA as a Biomarker for Hepatocellular Carcinoma." Clin. Chem., Jul. 24, 2008, 54:1664-1672.

Di Gioia et al., "Quantitative evaluation of RASSF1A methylation in the non-lesional, regenerative and neoplastic liver," BMC Cancer, 2006, 6:89, 12 pages.

Dill et al., "Immunoassays based on electrochemical detection using microelectrode arrays," Biosensors and Bioelectronics, 2004, 20:736-742.

Fischer et al., "Prognostic significance of RASSF1A promoter methylation on survival of non-small cell lung cancer patients treated with gemcitabine," Lung Cancer, 2007, 56:115-123.

Froehler et al., "Synthesis of DNA via deoxynucleoside H-phosphonate intermediates," Nucl. Acid Res., 1986, 14:5399-5407.

Gaffney et al., "Large-scale oligonucleotides synthesis by the H-Phosphonate method," Tet. Let., 1988, 29:2619-2622.

Garegg et al., "Nucleoside H-phosphonates III. Chemical synthesis of oligodeoxyribonucleotides by the hydrogenphosphonate approach," Tet. Let., 1986, 27:4051-4054.

Garegg et al., "Nucleoside H-phosphonates IV. Automated solid phase synthesis of oligoribonucleotides by the hydrogenphosphonate approach," Tet. Let., 27:4055-4058 (1986).

GenBank® Accession No. AJ536123; GenBank® GI No. 40643613, Nov. 14, 2006, 3 pages.

GenBank® Accession No. AJ536131; GenBank® GI No. 40643629, Nov. 14, 2006, 3 pages.

GenBank® Accession No. AJ536135; GenBank® GI No. 40643637, Nov. 14, 2006, 4 pages.

GenBank® Accession No. BA000007 GenBank® GI No. 47118301, Jan. 18, 2008, p. 1 of 157.

GenBank® Accession No. CP000052; GenBank® GI No. 761681535 Mar. 2010, 4 pages.

GenBank® Accession No. NC_002952 GenBank® GI No. 49482253, Jan. 22, 2012, p. 1 of 109.

GenBank® Accession No. NC_000962; GenBank® GI No. 5711668119 Jan. 2012, 2 pages.

GenBank® Accession No. NC_001803; GenBank® GI No. 9629367, Nov. 22, 2009, 8 pages.

GenBank® Accession No. NC_002016; GenBank® GI No. 8486122, Jul. 16, 2008, 2 pages.

GenBank® Accession No. NC_002695; GenBank® GI No. 15829254 at 1267936-1268205, Jan. 25, 2012, p. 1 of 178.

GenBank® Accession No. NC_002946; GenBank® GI No. 59800473, Jan. 20, 2012, p. 1 of 285 pages.

GenBank® Accession No. NC_003198; GenBank® GI No. 16758993, Jan. 20, 2012, 1 page.

GenBank® Accession No. NC_003210; GenBank® GI No. 16802048, Jan. 20, 2012, 1 page.

GenBank® Accession No. NC_003266; GenBank® GI No. 51527264, May 6, 2009, p. 1 of 21 pages.

GenBank® Accession No. NC_003485; GenBank® GI No. 19745201, Jan. 20, 2012, p. 1 of 350.

GenBank® Accession No. NC_003912; GenBank® GI No. 57236892, Aug. 1, 2011, p. 1 of 337.

GenBank® Accession No. NC_004603; GenBank® GI No. 28896774, Jan. 20, 2012, p. 1 of 441.

GenBank® Accession No. NC_007607; GenBank® GI No. 82524407, Apr. 1, 2010, p. 1 of 92.

GenBank® Accession No. NC_008533; GenBank® GI No. 116515308, Jan. 26, 2012, p. 1 of 383.

GenBank® Accession No. NC_010741; GenBank® GI No. 189025236, May 2, 2011, p. 1 of 174.

GenBank® Accession No. NC_013450; GenBank® GI No. 269201690, Feb. 14, 2012, p. 1 of 404.

GenBank® Accession No. NM_020469; GenBank® GI No. 58331215, Apr. 12, 2012, 4 pages.

GenBank® Accession No. X01712.1; GenBank® GI No. 59898, Apr. 18, 2005, 2 pages.

(56) References Cited

OTHER PUBLICATIONS

Guerini et al., "Rapid enrichment strategy for isolation of Listeria from bovine hide, carcass, and meat samples," J. Food Prot., 2007, 70(1):53-57.
He et al., "Selective and homogeneous fluorescent DNA detection by target-induced strand displacement using cationic conjugated polyelectrolytes," Anal. Chem., 2008, 80(6):2239-2243.
Jin et al., "Multiplexed bead-based mesofluidic system for detection of food-borne pathogenic bacteria," Appl. Environ. Microbiol., 2009, 75:6647-6654.
Kanagawa, "Bias and artifacts in multitemplate polymerase chain reactions (PCR)," J Biosci Bioeng., 2003, 96(4):317-323.
Kiesling et al., "Sequence specific detection of DNA using nicking endonuclease signal amplification (NESA)," Nucl Acid Res, 2007 35(18):e117.
Liu et al., "Electrochemical detection of hepatitis C virus based on site-specific DNA cleavage of BamHI endonuclease," Chem Commom (Camb), Apr. 7, 2009, (13):1635-1637.
Maruya et al., "Differential methylation status of tumor-associated genes in head and neck squamous carcinoma: incidence and potential implications," Clin. Cancer Res., 2004, 10:3825-3830.
McClelland et al., Effect of site-specific modification on restriction endonucleases and DNA modification methyltransferases, Nucleic Acids Res., 1994, 22:3640-3659.
Nam et al., "Evaluation of universal pre-enrichment broth for isolation of *Salmonella* spp., *Escherichia coli* O157:H7, and Listeria monocytogenes from dairy farm environmental samples." Foodborne Pathog. Dis., 2004, 1(1):37-44.
O'Mahony and Papkovsky, "Rapid high throughput assessment of aerobic bacteria in complex samples by fluorescence-based oxygen respirometry," Applied and Environmental Microbiology, 2006, 72:1279-1287.
O'Mahony et al., "Analysis of total aerobic viable counts in samples of raw meat using fluorescence-based probe and oxygen consumption assay," Food Control, 2009, 20:129-135.
Pei, D. et. al., "Site-specific cleavage of duplex DNA bv a semisynthetic nuclease via triple-helix formation," Proceedings of the National Academy of Sciences of the United States of America, vol. 87, No. 24, (1990), pp. 9858-9862.
Perelle et al., "A LightCycler real-time PCR hybridization probe assay for detecting food-borne thermophilic Campylobacter," Mol. Cell. Probes, 2004, 18:321-327.
Polz and Cavanaugh, "Bias in Template-to-Product Ratios in Multitemplate PCR," Applied and Environmental Microbiology, 1998, 64(10):3724-3730.
Rykova et al., "Methylation-Based Analysis of Circulating DNA for Breast Tumor Screening." Ann. N.Y. Acad. Sci., 2008, 1137:232-235.
Schrank et al., "Influence of enrichment media and application of a PCR based method to detect *Salmonella* in poultry industry products and clinical samples," Vet. Micro., 2001, 82:45-53.
Sipos et al., "Effect of primer mismatch, annealing temperature and PCR cycle number on 16S rRNA gene-targeting bacterial community analysis," FEMS Microbiol Ecol., 2007, 60(2):341-350.
Sud'ina et al., "Affinity Modification of the Restriction Endonuclease SsoII by 2'—Aldehyde-Containing Double Stranded DNAs," Biochemistry (Moscow), vol. 70, No. 8, 2005, pp. 941-947.
Sunami et al., "Analysis of methylated circulating DNA in cancer patients' blood," Methods Mol. Biol., 2009, 507:349-356.
Szyf, "Targeting DNA methylation in cancer," Ageing Res. Rev., 2003, 2(3):299-328.
Urdea, "Synthesis and characterization of branched DNA (BDNA) for the direct and quantitative detection of CMV, HBV, HCV, and HIV," Clinical Chemistry, 1993, 39(4):725-726.
Wang et al., "Human thiopurine S-methyltransferase pharmacogenetics: Variant allozyme misfolding and aggresome formation," Proc. Natl. Acad. Sci. USA, 2005, 102(26):9394-9399, Published online before print Jun. 20, 2005.
Wang et al., "Identification of epigenetic aberrant promoter methylation of RASSF1A in serum DNA and its clinicopathological significance in lung cancer," Lung Cancer, 2007, 56:289-294.
Weisenberger et al., "DNA methylation analysis by digital bisulfate genomic sequencing and digital MethyLight," Nucl Acid Res., 2008, 36(14):4689-4698.
Widschwendter et al., "Epigenotyping in peripheral blood cell DNA and breast cancer risk: a proof of principle study," PLoS ONE, 2008, 3(7):e2656.
Yeo et al., "High frequency of promoter hypermethylation of RASSF1A in tumorous and non-tumorous tissue of breast cancer," Pathology, 2005, 37:125-130.
Zhang et al., "Genetic diversity of intimin genes of attaching and effacing *Escherichia coli* strains," J. Clin. Microbiol., 2002, 40:4486-4492.
U.S. Appl. No. 12/535,017, filed Aug. 4, 2009, Smith, Issued.
U.S. Appl. No. 13/027,887, filed Feb. 15, 2011, Smith, Issued.
U.S. Appl. No. 13/027,919, filed Feb. 15, 2011, Smith, Issued.
U.S. Appl. No. 13/027,980, filed Feb. 15, 2011, Smith, Issued.
U.S. Appl. No. 13/028,021, filed Feb. 15, 2011, Smith, Issued.
U.S. Appl. No. 13/603,257, filed Sep. 4, 2012, Smith, Issued.
U.S. Appl. No. 14/046,389, filed Oct. 4, 2013, Smith, Issued.
U.S. Appl. No. 14/080,388, filed Nov. 14, 2013, Smith, Issued.
U.S. Appl. No. 14/090,167, filed Nov. 26, 2013, Smith, Issued.
U.S. Appl. No. 14/135,121, filed Dec. 19, 2013, Smith, Issued.
U.S. Appl. No. 14/487,978, filed Sep. 16, 2014, Smith, Issued.
U.S. Appl. No. 14/627,742, filed Feb. 20, 2015, Smith, Published.
U.S. Appl. No. 14/841,015, filed Aug. 31, 2015, Smith, Issued.
U.S. Appl. No. 14/841,282, filed Aug. 31, 2015, Smith, Issued.
U.S. Appl. No. 14/841,289, filed Aug. 31, 2015, Smith, Issued.
U.S. Appl. No. 15/218,415, filed Jul. 25, 2016, Smith, Issued.
U.S. Appl. No. 15/225,365, filed Aug. 1, 2016, Smith, Issued.
U.S. Appl. No. 15/587,944, filed May 5, 2017, Smith, Issued.
U.S. Appl. No. 15/604,112, filed May 24, 2017, Smith, Issued.
U.S. Appl. No. 16/146,419, filed Sep. 28, 2018, Smith, Published.
U.S. Appl. No. 16/212,427, filed Dec. 6, 2018, Smith, Published.
U.S. Appl. No. 16/448,784, filed Jun. 21, 2019, Smith, Published.

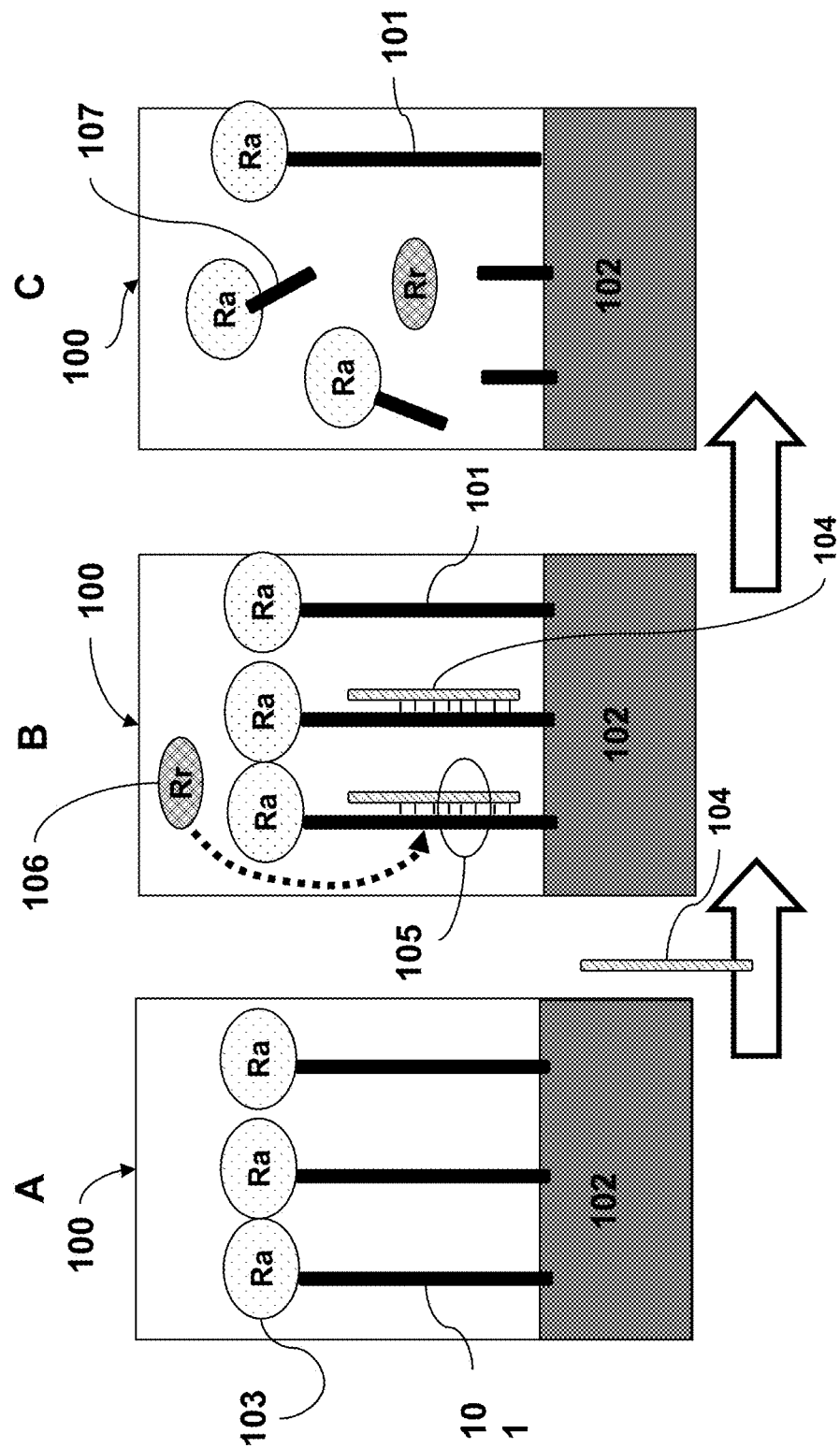

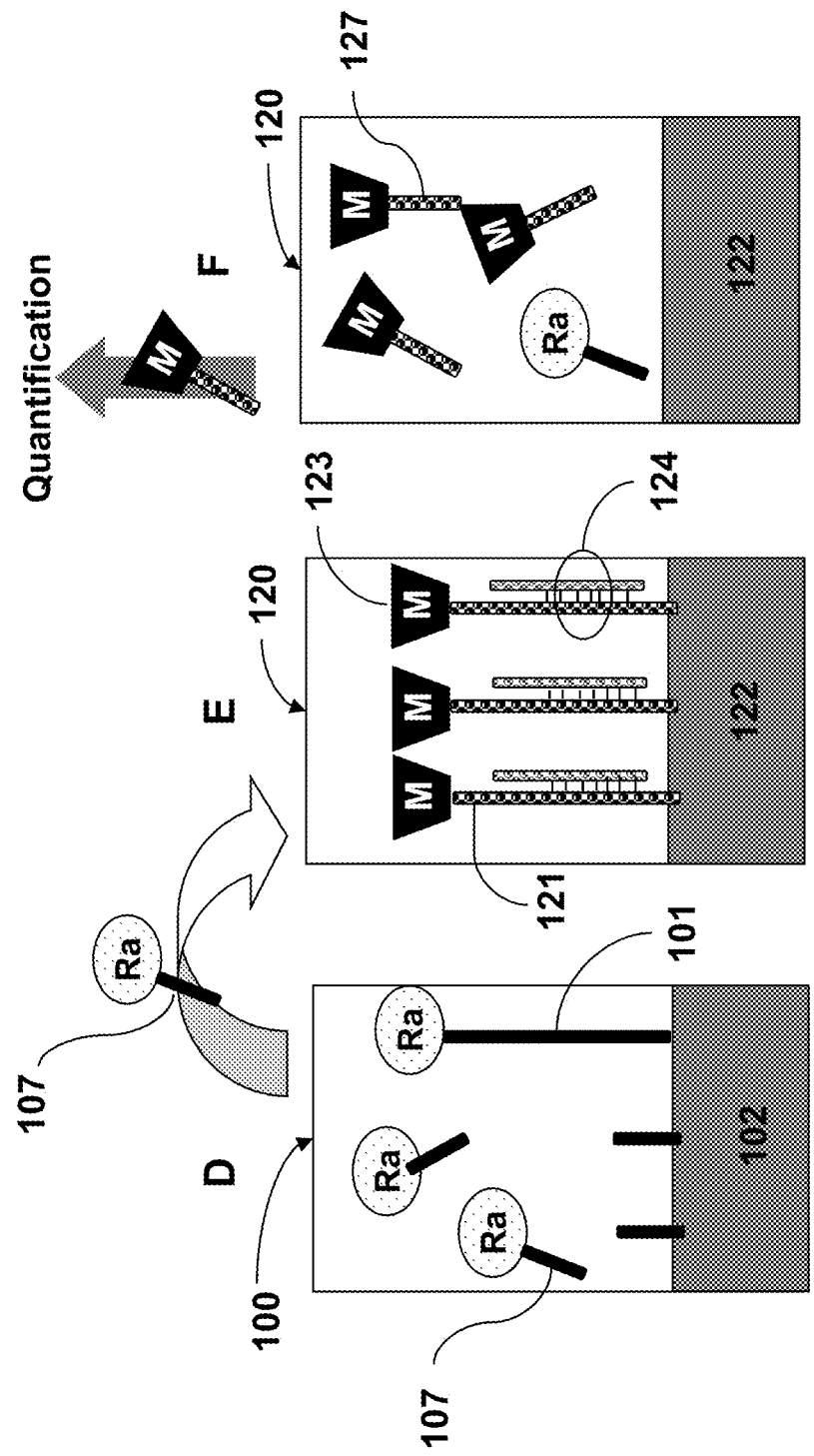
Figure 1 con't

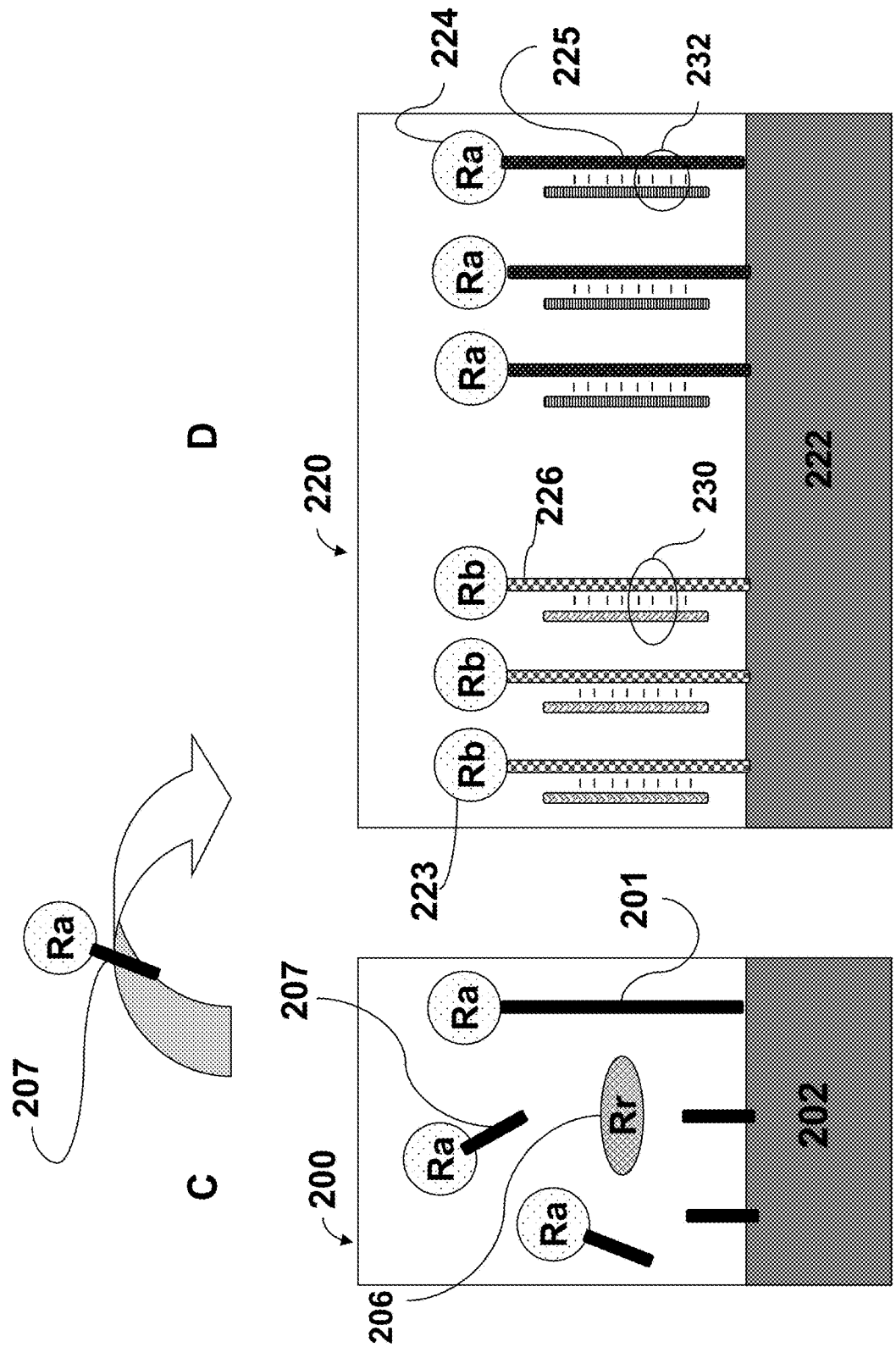
Figure 3 con't

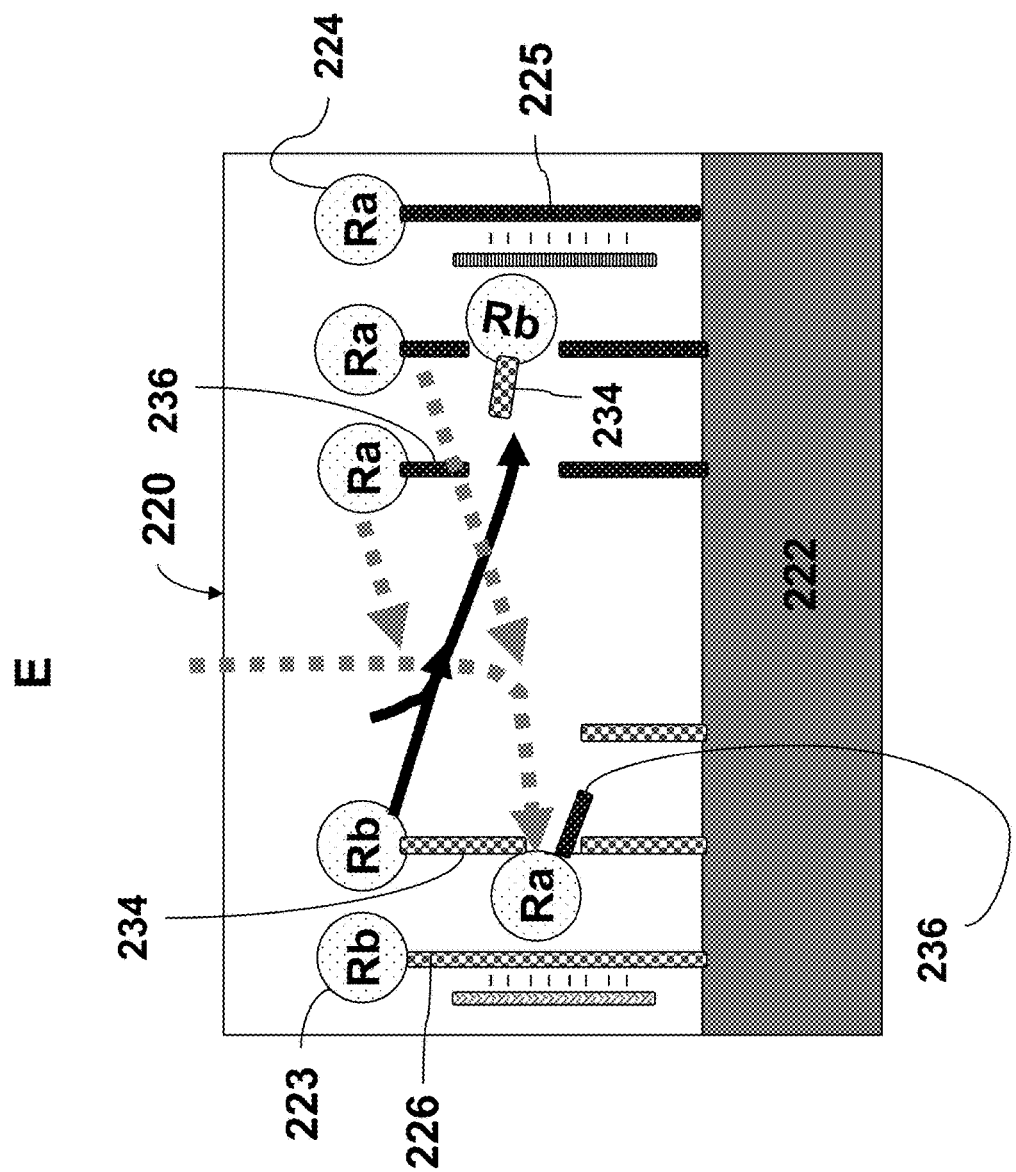

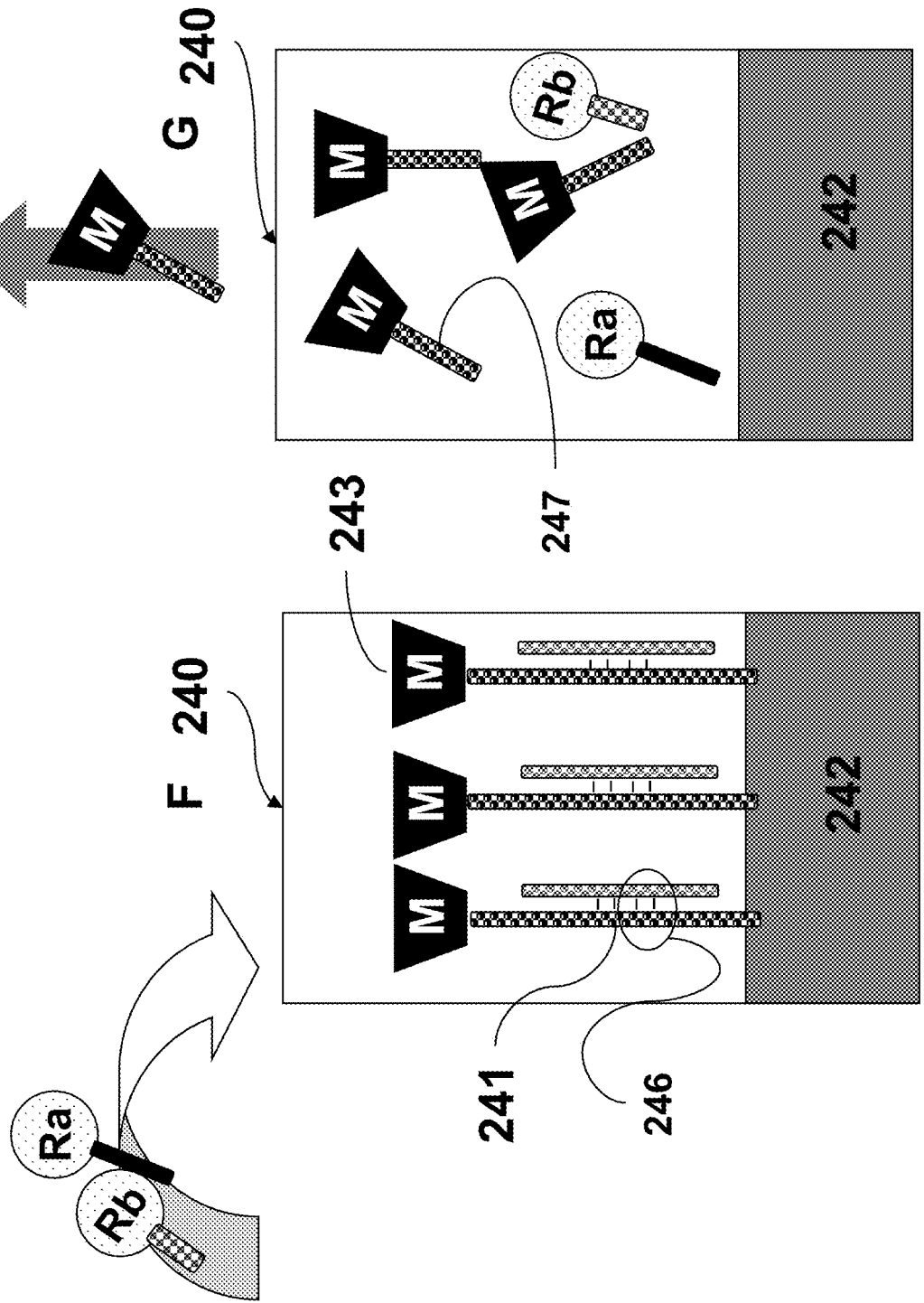

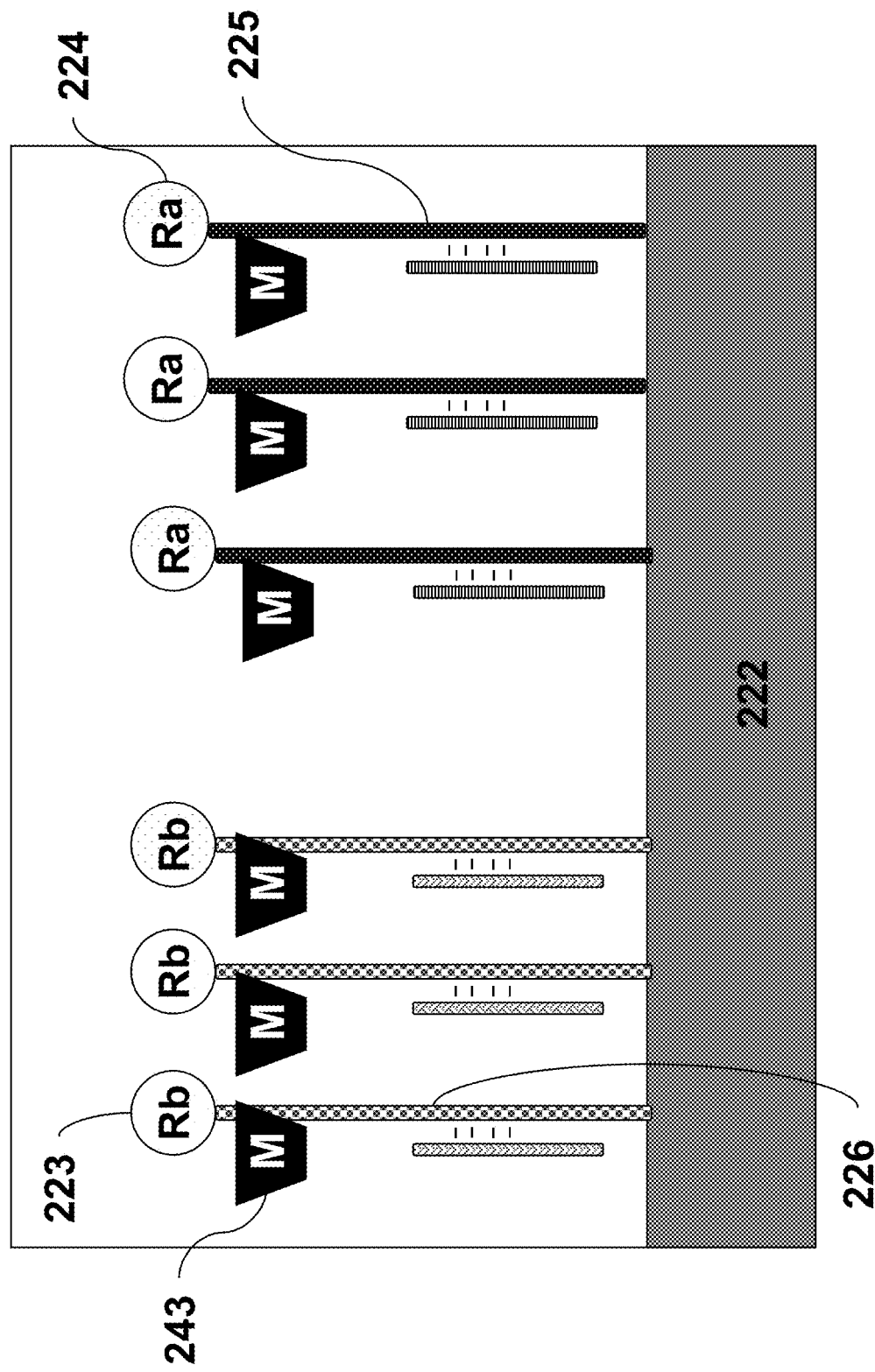

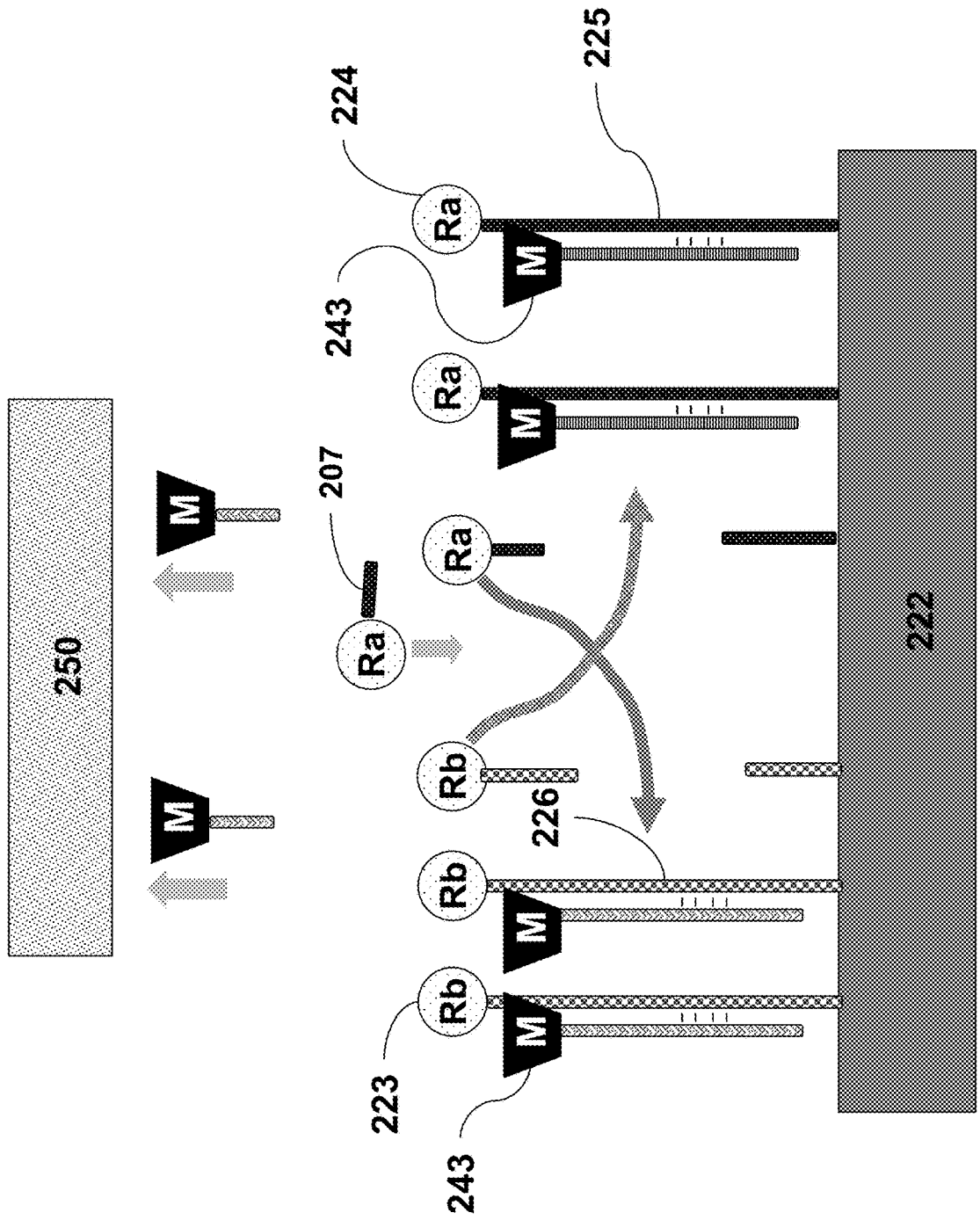

DETECTING NUCLEIC ACID

CROSS-REFERENCE TO RELATED APPLICATIONS

This application is a continuation of U.S. patent application Ser. No. 15/587,944, filed May 5, 2017, which is a continuation of U.S. patent application Ser. No. 14/487,978, filed Sep. 16, 2014 (now U.S. Pat. No. 9,677,120), which is a continuation of U.S. patent application Ser. No. 14/135,121, filed Dec. 19, 2013 (now U.S. Pat. No. 8,865,407), which is a continuation of U.S. patent application Ser. No. 13/603,257, filed Sep. 4, 2012 (now U.S. Pat. No. 8,632,974), which is a continuation of U.S. patent application Ser. No. 12/535,017, filed Aug. 4, 2009 (now U.S. Pat. No. 8,278,048), which claims the benefit of priority of U.S. Provisional Application Ser. No. 61/166,843, filed Apr. 6, 2009, and U.S. Provisional Application Ser. No. 61/089,392, filed Aug. 15, 2008. The disclosures of the prior applications are considered part of (and are incorporated by reference in) the disclosure of this application.

BACKGROUND

1. Technical Field

This document relates to methods and materials involved in detecting nucleic acid. For example, this document relates to methods and materials involved in using an enzymatic amplification cascade of restriction endonucleases to detect nucleic acid.

2. Background

The polymerase chain reaction (PCR) is a technique commonly used to amplify and detect nucleic acid. For example, real-time PCR can be used to amplify and detect small amounts of template DNA present in a sample. Typically, PCR involves adding a nucleic acid primer pair and a heat-stable DNA polymerase, such as Taq polymerase, to a sample believed to contain a targeted nucleic acid to be amplified. Subjecting the sample containing the primer pair and polymerase to a thermal cycling process sets in motion a chain reaction in which the targeted DNA template located between the primers is exponentially amplified. The presence of this amplified template can be detected using techniques such as gel electrophoresis or the amount of amplified template can be assessed using techniques such as those involving the use of fluorescently labeled probes.

SUMMARY

This document provides methods and materials for detecting target nucleic acid. For example, this document provides methods and materials for detecting the presence or absence of target nucleic acid within a sample, methods and materials for detecting the amount of target nucleic acid present within a sample, kits for detecting the presence or absence of target nucleic acid within a sample, kits for detecting the amount of target nucleic acid present within a sample, and methods for making such kits. In general, the methods and materials provided herein can include performing an enzymatic amplification cascade of restriction endonucleases as described herein to detect target nucleic acid in a manner that is rapid, inexpensive, sensitive, and specific. In some cases, the methods and materials provided herein can be used in addition to or can replace current PCR-based nucleic acid detection approaches.

The methods and materials provided herein can allow clinicians, medical professionals, laboratory personnel, and researchers to detect any type of target nucleic acid. For example, the methods and materials provided herein can be used in genotyping applications to detect nucleic acid mutations (e.g., single nucleotide polymorphisms (SNPs)), genome rearrangements, and genome epigenetic events (e.g., DNA methylation events), can be used in diagnostic or prognostic applications to detect viruses or microorganisms (e.g., bacteria, fungi, and protozoa), can be used in gene expression applications to detect mRNA levels within particular cell types, and can be used in forensic applications to compare the identity between samples or to assess a sample's origin. In some cases, the methods and materials provided herein can be used by individuals outside the medical/biotechnology profession to detect target nucleic acid. For example, a kit provided herein for detecting the presence of bacteria (e.g., *E. coli*) can be designed for use as a home detection kit such that a user can detect the presence or absence of *E. coli* nucleic acid within a biological sample (e.g., blood sample, mucus sample, or saliva sample) obtained from the user.

In general, one aspect of this document features a method for assessing a sample for target nucleic acid. The method comprises, or consists essentially of: (a) contacting the sample with a probe nucleic acid comprising an amplifying restriction endonuclease and a nucleotide sequence complementary to a sequence of the target nucleic acid under conditions wherein, if the target nucleic acid is present in the sample, at least a portion of the target nucleic acid hybridizes to at least a portion of the probe nucleic acid to form a double-stranded portion of nucleic acid comprising a restriction endonuclease cut site, (b) contacting the double-stranded portion of nucleic acid with a recognition restriction endonuclease having the ability to cut the double-stranded portion of nucleic acid at the restriction endonuclease cut site under conditions wherein the recognition restriction endonuclease cleaves the double-stranded portion of nucleic acid at the restriction endonuclease cut site, thereby separating a portion of the probe nucleic acid comprising the amplifying restriction endonuclease from at least another portion of the probe nucleic acid, (c) contacting the portion of the probe nucleic acid comprising the amplifying restriction endonuclease with a reporter nucleic acid comprising a double-stranded portion of nucleic acid comprising a restriction endonuclease cut site of the amplifying restriction endonuclease under conditions wherein the amplifying restriction endonuclease cleaves the reporter nucleic acid at the restriction endonuclease cut site of the amplifying restriction endonuclease, thereby separating a portion of the reporter nucleic acid from at least another portion of the reporter nucleic acid, and (d) determining the presence or absence of the portion of the reporter nucleic acid, wherein the presence of the portion of the reporter nucleic acid indicates that the sample contains the target nucleic acid, and wherein the absence of the portion of the reporter nucleic acid indicates that the sample does not contain the target nucleic acid. The probe nucleic acid can be single-stranded probe nucleic acid. The probe nucleic acid can be attached to a solid support. The probe nucleic acid can be directly attached to a solid support. The portion of the probe nucleic acid comprising the amplifying restriction endonuclease can be released from the solid support via step (b). Step (a) and step (b) can be performed in the same compartment. Step (a) and step (b) can be performed in a first compartment, and step (c) can be performed in a second compartment. Step (a) and step (b) can be performed by adding the sample to a compartment comprising the probe nucleic acid and the recognition restriction endonuclease. The probe nucleic acid can comprise (i) a single-stranded portion comprising the nucleotide sequence complementary to the sequence of the target nucleic acid and (ii) a double-stranded portion. The probe nucleic acid can comprise a first nucleic acid strand, which can comprise the nucleotide sequence complementary to the sequence of the target nucleic acid, hybridized to a second nucleic acid strand comprising the amplifying restriction endonuclease. The first nucleic acid strand can be attached to a solid support. The first nucleic acid strand can be directly attached to a solid support. A portion of the second nucleic acid strand can be hybridized with the first nucleic acid strand to form the double-stranded portion. The portion of the probe nucleic acid comprising the amplifying restriction endonuclease that is separated from the at least another portion of the probe nucleic acid in step (b) can comprise a portion of the first nucleic acid strand and all of the second strand. The portion of the probe nucleic acid comprising the amplifying restriction endonuclease that is separated from the at least another portion of the probe nucleic acid in step (b) can comprise at least a portion of the target nucleic acid. The method can comprise using a plurality of the probe nucleic acid in step (a). The method can comprise using a plurality of the reporter nucleic acid in step (c). The reporter nucleic acid in step (c) can be in molar excess of the portion of the probe nucleic acid comprising the amplifying restriction endonuclease from the step (b). The number of molecules of the portion of the probe nucleic acid comprising the amplifying restriction endonuclease that is separated from the at least another portion of the probe nucleic acid in step (b) can be in an essentially linear relationship to the number of molecules of the target nucleic acid present in the sample. The reporter nucleic acid can be attached to a solid support. The reporter nucleic acid can be directly attached to a solid support. The reporter nucleic acid can comprise a single-stranded portion of nucleic acid. The reporter nucleic acid can comprise a label. The label can be a fluorescent label, a radioactive label, an enzyme label, or a redox label. The portion of the reporter nucleic acid that is separated from the at least another portion of the reporter nucleic acid can comprise the label. The reporter nucleic acid can comprise a first nucleic acid strand, which can comprise the label, hybridized to a second nucleic acid strand. The second nucleic acid strand can be attached to a solid support. The second nucleic acid strand can be directly attached to a solid support. A portion of the first nucleic acid strand can hybridize with the second nucleic acid strand to form the double-stranded portion of nucleic acid comprising the restriction endonuclease cut site of the amplifying restriction endonuclease. The reporter nucleic acid can comprise a third nucleic acid strand. The third nucleic acid strand can hybridize with the second nucleic acid strand to form the double-stranded portion of nucleic acid comprising the restriction endonuclease cut site of the amplifying restriction endonuclease. The reporter nucleic acid can be attached to a solid support, and the portion of the reporter nucleic acid that is separated from the at least another portion of the reporter nucleic acid and that comprises the label can be released from the solid support via step (c). Determining step (d) can comprise detecting the label. The label can be a fluorescent label, and determining step (d) can comprise detecting the fluorescent label. Determining step (d) can comprise detecting the portion of the reporter nucleic acid separated from the at least another portion of the reporter nucleic acid using a capillary electrophoresis technique. Steps (a), (b), and (c) can be performed without nucleic acid amplification. Steps (a), (b), (c), and (d) can be performed without nucleic acid amplification. The determining step can comprise determining the amount of the target nucleic acid present within the sample.

In another aspect, this document features a method for assessing a sample for target nucleic acid. The method comprises, or consists essentially of, (a) contacting the sample with a probe nucleic acid comprising an initial amplifying restriction endonuclease and a nucleotide sequence complementary to a sequence of the target nucleic acid under conditions wherein, if the target nucleic acid is present in the sample, at least a portion of the target nucleic acid hybridizes to at least a portion of the probe nucleic acid to form a double-stranded portion of nucleic acid comprising a restriction endonuclease cut site, (b) contacting the double-stranded portion of nucleic acid with a recognition restriction endonuclease having the ability to cut the double-stranded portion of nucleic acid at the restriction endonuclease cut site under conditions wherein the recognition restriction endonuclease cleaves the double-stranded portion of nucleic acid at the restriction endonuclease cut site, thereby separating a portion of the probe nucleic acid comprising the initial amplifying restriction endonuclease from at least another portion of the probe nucleic acid, (c) contacting the portion of the probe nucleic acid comprising the initial amplifying restriction endonuclease with a first signal expansion nucleic acid comprising a secondary amplifying restriction endonuclease and a double-stranded portion of nucleic acid comprising a restriction endonuclease cut site of the initial amplifying restriction endonuclease under conditions wherein the initial amplifying restriction endonuclease cleaves the first signal expansion nucleic acid at the restriction endonuclease cut site of the initial amplifying restriction endonuclease, thereby separating a portion of the first signal expansion nucleic acid comprising the secondary amplifying restriction endonuclease from at least another portion of the first nucleic acid, (d) contacting the portion of the first signal expansion nucleic acid comprising the secondary amplifying restriction endonuclease with a second signal expansion nucleic acid comprising the initial amplifying restriction endonuclease and a double-stranded portion of nucleic acid comprising a restriction endonuclease cut site of the secondary amplifying restriction endonuclease under conditions wherein the secondary amplifying restriction endonuclease cleaves the second signal expansion nucleic acid at the restriction endonuclease cut site of the secondary amplifying restriction endonuclease, thereby separating a portion of the second signal expansion nucleic acid comprising the initial amplifying restriction endonuclease from at least another portion of the second signal expansion nucleic acid, (e) contacting (i) the portion of the probe nucleic acid comprising the initial amplifying restriction endonuclease, (ii) the portion of the second signal expansion nucleic acid comprising the initial amplifying restriction endonuclease, (iii) the portion of the first signal expansion nucleic acid comprising the secondary amplifying restriction endonuclease, or (iv) any combination thereof with a reporter nucleic acid comprising a double-stranded portion of nucleic acid comprising a restriction endonuclease cut site of the initial amplifying restriction endonuclease and/or a restriction endonuclease cut site of the secondary amplifying restriction endonuclease under conditions wherein the initial amplifying restriction endonuclease cleaves the reporter nucleic acid at the restriction endonuclease cut site of the initial amplifying restriction endonuclease, thereby separating a portion of the reporter nucleic acid from at least another portion of the reporter nucleic acid, and (f) determining the presence or absence of the portion of the reporter nucleic acid, wherein the presence of the portion of the reporter nucleic acid indicates that the sample contains the target nucleic acid, and wherein the absence of the portion of the reporter nucleic acid indicates that the sample does not contain the target nucleic acid. The probe nucleic acid can be single-stranded probe nucleic acid. The probe nucleic acid can be attached to a solid support. The probe nucleic acid can be directly attached to a solid support. The portion of the probe nucleic acid comprising the initial amplifying restriction endonuclease can be released from the solid support via step (b). Step (a) and step (b) can be performed in the same compartment. Step (c) and step (d) can be performed in the same compartment. Step (a) and step (b) can be performed in a first compartment, and step (c) and step (d) can be performed in a second compartment. Step (a) and step (b) can be performed by adding the sample to a compartment comprising the probe nucleic acid and the recognition restriction endonuclease. Step (c) and step (d) can be performed by adding the portion of the probe nucleic acid comprising the initial amplifying restriction endonuclease to a compartment comprising the first signal expansion nucleic acid and the second signal expansion nucleic acid. The probe nucleic acid can comprise (i) a single-stranded portion comprising the nucleotide sequence complementary to the sequence of the target nucleic acid and (ii) a double-stranded portion. The probe nucleic acid can comprise a first nucleic acid strand, which can comprise the nucleotide sequence complementary to the sequence of the target nucleic acid, hybridized to a second nucleic acid strand comprising the initial amplifying restriction endonuclease. The first nucleic acid strand can be attached to a solid support. The first nucleic acid strand can be directly attached to a solid support. A portion of the second nucleic acid strand can be hybridized with the first nucleic acid strand to form the double-stranded portion. The portion of the probe nucleic acid comprising the initial amplifying restriction endonuclease that is separated from the at least another portion of the probe nucleic acid in step (b) can comprise a portion of the first nucleic acid strand and all of the second strand. The portion of the probe nucleic acid comprising the initial amplifying restriction endonuclease that is separated from the at least another portion of the probe nucleic acid in step (b) can comprise at least a portion of the target nucleic acid. The method can comprise using a plurality of the probe nucleic acid in step (a). The method can comprise using a plurality of the reporter nucleic acid in step (e). The reporter nucleic acid in step (e) can be in molar excess of the portion of the probe nucleic acid comprising the initial amplifying restriction endonuclease from step (b). The number of molecules of the portion of the probe nucleic acid comprising the initial amplifying restriction endonuclease that is separated from the at least another portion of the probe nucleic acid in step (b) can be in an essentially linear relationship to the number of molecules of the target nucleic acid present in the sample. The first signal expansion nucleic acid and the second signal expansion nucleic acid can be attached to a solid support. The first signal expansion nucleic acid and the second signal expansion nucleic acid can be directly attached to a solid support. The first signal expansion nucleic acid and the second signal expansion nucleic acid can be attached to a solid support in the same compartment. The portion of the first signal expansion nucleic acid comprising the secondary amplifying restriction endonuclease can be released from the solid support via step (c). The portion of the second signal expansion nucleic acid comprising the initial amplifying restriction endonuclease can be released from the solid support via step (d). The first signal expansion nucleic acid can comprise a first nucleic acid strand, which can comprise the secondary amplifying restriction endonuclease, hybridized to a second nucleic acid strand to form the double-stranded portion of nucleic acid comprising the restriction endonuclease cut site of the initial amplifying restriction endonuclease. The first nucleic acid strand can be attached to a solid support. The first nucleic acid strand can be directly attached to a solid support. The second nucleic acid strand can be attached to a solid support. The second nucleic acid strand can be directly attached to a solid support. The second signal expansion nucleic acid can comprise a first nucleic acid strand, which can comprise the initial amplifying restriction endonuclease, hybridized to a second nucleic acid strand to form the double-stranded portion of nucleic acid comprising the restriction endonuclease cut site of the secondary amplifying restriction endonuclease. The first nucleic acid strand can be attached to a solid support. The first nucleic acid strand can be directly attached to a solid support. The second nucleic acid strand can be attached to a solid support. The second nucleic acid strand can be directly attached to a solid support. The reporter nucleic acid can be attached to a solid support. The reporter nucleic acid can be directly attached to a solid support. The reporter nucleic acid can comprise a single-stranded portion of nucleic acid. The reporter nucleic acid can comprise a label. The label can be a fluorescent label, a radioactive label, an enzyme label, or a redox label. The portion of the reporter nucleic acid that is separated from the at least another portion of the reporter nucleic acid can comprise the label. The reporter nucleic acid can comprise a first nucleic acid strand, which can comprise the label, hybridized to a second nucleic acid strand. The second nucleic acid strand can be attached to a solid support. The second nucleic acid strand can be directly attached to a solid support. A portion of the first nucleic acid strand can hybridize with the second nucleic acid strand to form the double-stranded portion of nucleic acid comprising the restriction endonuclease cut site of the initial amplifying restriction endonuclease. The reporter nucleic acid can comprise a third nucleic acid strand. The third nucleic acid strand can be hybridized with the second nucleic acid strand to form the double-stranded portion of nucleic acid comprising the restriction endonuclease cut site of the initial amplifying restriction endonuclease. The reporter nucleic acid can be attached to a solid support, and the portion of the reporter nucleic acid that is separated from the at least another portion of the reporter nucleic acid and that comprises the label can be released from the solid support via step (e). Determining step (f) can comprise detecting the label. The label can be a fluorescent label, and determining step (f) can comprise detecting the fluorescent label. Determining step (f) can comprise detecting the portion of the reporter nucleic acid separated from the at least another portion of the reporter nucleic acid using a capillary electrophoresis technique. Steps (a), (b), (c), (d), and (e) can be performed without nucleic acid amplification. Steps (a), (b), (c), (d), (e), and (f) can be performed without nucleic acid amplification. The determining step can comprise determining the amount of the target nucleic acid present within the sample.

In another aspect, this document features a method for assessing a sample for target nucleic acid. The method comprises, or consists essentially of, (a) contacting the sample with a probe nucleic acid comprising an initial amplifying restriction endonuclease and a nucleotide sequence complementary to a sequence of the target nucleic acid under conditions wherein, if the target nucleic acid is present in the sample, at least a portion of the target nucleic acid hybridizes to at least a portion of the probe nucleic acid to form a double-stranded portion of nucleic acid comprising a restriction endonuclease cut site, (b) contacting the double-stranded portion of nucleic acid with a recognition restriction endonuclease having the ability to cut the double-stranded portion of nucleic acid at the restriction endonuclease cut site under conditions wherein the recognition restriction endonuclease cleaves the double-stranded portion of nucleic acid at the restriction endonuclease cut site, thereby separating a portion of the probe nucleic acid comprising the initial amplifying restriction endonuclease from at least another portion of the probe nucleic acid, (c) contacting the portion of the probe nucleic acid comprising the initial amplifying restriction endonuclease with a first reporter nucleic acid (or a first signal expansion nucleic acid) comprising a secondary amplifying restriction endonuclease and a double-stranded portion of nucleic acid comprising a restriction endonuclease cut site of the initial amplifying restriction endonuclease under conditions wherein the initial amplifying restriction endonuclease cleaves the first reporter nucleic acid at the restriction endonuclease cut site of the initial amplifying restriction endonuclease, thereby separating a portion of the first nucleic acid comprising the secondary amplifying restriction endonuclease from at least another portion of the first nucleic acid, (d) contacting the portion of the first reporter nucleic acid comprising the secondary amplifying restriction endonuclease with a second reporter nucleic acid (or a second signal expansion nucleic acid) comprising the initial amplifying restriction endonuclease and a double-stranded portion of nucleic acid comprising a restriction endonuclease cut site of the secondary amplifying restriction endonuclease under conditions wherein the initial amplifying restriction endonuclease cleaves the second nucleic acid at the restriction endonuclease cut site of the secondary amplifying restriction endonuclease, thereby separating a portion of the second nucleic acid comprising the initial amplifying restriction endonuclease from at least another portion of the second nucleic acid, and (e) determining the presence or absence of the portion of the first reporter nucleic acid, the second reporter nucleic acid, or both the first reporter nucleic acid and the second reporter nucleic acid, wherein the presence indicates that the sample contains the target nucleic acid, and wherein the absence indicates that the sample does not contain the target nucleic acid. The probe nucleic acid can be single-stranded probe nucleic acid. The probe nucleic acid can be attached to a solid support. The probe nucleic acid can be directly attached to a solid support. The portion of the probe nucleic acid comprising the initial amplifying restriction endonuclease can be released from the solid support via step (b). Step (a) and step (b) can be performed in the same compartment. Step (c) and step (d) can be performed in the same compartment. Step (a) and step (b) can be performed in a first compartment, and step (c) and step (d) can be performed in a second compartment. Step (a) and step (b) can be performed by adding the sample to a compartment comprising the probe nucleic acid and the recognition restriction endonuclease. Step (c) and step (d) can be performed by adding the portion of the probe nucleic acid comprising the initial amplifying restriction endonuclease to a compartment comprising the first reporter nucleic acid and the second reporter nucleic acid. The probe nucleic acid can comprise (i) a single-stranded portion comprising the nucleotide sequence complementary to the sequence of the target nucleic acid and (ii) a double-stranded portion. The probe nucleic acid can comprise a first nucleic acid strand, which can comprise the nucleotide sequence complementary to the sequence of the target nucleic acid, hybridized to a second nucleic acid strand comprising the initial amplifying restriction endonuclease. The first nucleic acid strand can be attached to a solid support. The first nucleic acid strand can be directly attached to a solid support. A portion of the second nucleic acid strand can be hybridized with the first nucleic acid strand to form the double-stranded portion. The portion of the probe nucleic acid comprising the initial amplifying restriction endonuclease that is separated from the at least another portion of the probe nucleic acid in step (b) can comprise a portion of the first nucleic acid strand and all of the second strand. The portion of the probe nucleic acid comprising the initial amplifying restriction endonuclease that is separated from the at least another portion of the probe nucleic acid in step (b) can comprise at least a portion of the target nucleic acid. The method can comprise using a plurality of the probe nucleic acid in step (a). The method can comprise using a plurality of the first reporter nucleic acid in step (c). The first reporter nucleic acid in step (c) can be in molar excess of the portion of the probe nucleic acid comprising the initial amplifying restriction endonuclease from step (b). The method can comprise using a plurality of the second reporter nucleic acid in step (d). The second reporter nucleic acid in step (d) can be in molar excess of the portion of the probe nucleic acid comprising the initial amplifying restriction endonuclease from step (b). The number of molecules of the portion of the probe nucleic acid comprising the initial amplifying restriction endonuclease that is separated from the at least another portion of the probe nucleic acid in step (b) can be in an essentially linear relationship to the number of molecules of the target nucleic acid present in the sample. The first reporter nucleic acid and the second reporter nucleic acid can be attached to a solid support. The first reporter nucleic acid and the second reporter nucleic acid can be directly attached to a solid support. The first reporter nucleic acid and the second reporter nucleic acid can be attached to a solid support in the same compartment. The portion of the first reporter nucleic acid comprising the secondary amplifying restriction endonuclease can be released from the solid support via step (c). The portion of the second reporter nucleic acid comprising the initial amplifying restriction endonuclease can be released from the solid support via step (d). The first reporter nucleic acid can comprise a label. The label can be a fluorescent label, a radioactive label, an enzyme label, or a redox label. The second reporter nucleic acid can comprise a label. The label can be a fluorescent label, a radioactive label, an enzyme label, or a redox label. The first reporter nucleic acid and the second reporter nucleic acid can comprise a label. The first reporter nucleic acid and the second reporter nucleic acid can comprise the same label. The label can be a fluorescent label, a radioactive label, an enzyme label, or a redox label. The first reporter nucleic acid can be attached to a solid support, wherein the portion of the first reporter nucleic acid that is separated from the at least another portion of the first reporter nucleic acid comprises a label, and wherein the portion of the first reporter nucleic acid that is separated from the at least another portion of the first reporter nucleic acid and that comprises the label is released from the solid support via step (c). The first reporter nucleic acid can comprise a first nucleic acid strand, which can comprise the secondary amplifying restriction endonuclease, hybridized to a second nucleic acid strand to form the double-stranded portion of nucleic acid comprising the restriction endonuclease cut site of the initial amplifying restriction endonuclease. The first nucleic acid strand can be attached to a solid support. The first nucleic acid strand can be directly attached to a solid support. The second nucleic acid strand can be attached to a solid support. The second nucleic acid strand can be directly attached to a solid support. The first nucleic acid strand can comprise a label. The label can be a fluorescent label, a radioactive label, an enzyme label, or a redox label. The second nucleic acid strand can comprise a label. The label can be a fluorescent label, a radioactive label, an enzyme label, or a redox label. The second reporter nucleic acid can be attached to a solid support, wherein the portion of the second reporter nucleic acid that is separated from the at least another portion of the second reporter nucleic acid comprises a label, and wherein the portion of the second reporter nucleic acid that is separated from the at least another portion of the second reporter nucleic acid and that comprises the label is released from the solid support via step (d). The second reporter nucleic acid can comprise a first nucleic acid strand, which can comprise the initial amplifying restriction endonuclease, hybridized to a second nucleic acid strand to form the double-stranded portion of nucleic acid comprising the restriction endonuclease cut site of the secondary amplifying restriction endonuclease. The first nucleic acid strand can be attached to a solid support. The first nucleic acid strand can be directly attached to a solid support. The second nucleic acid strand can be attached to a solid support. The second nucleic acid strand can be directly attached to a solid support. The first nucleic acid strand can comprise a label. The label can be a fluorescent label, a radioactive label, an enzyme label, or a redox label. The second nucleic acid strand can comprise a label. The label can be a fluorescent label, a radioactive label, an enzyme label, or a redox label. The portion of the first reporter nucleic acid separated from the at least another portion of the first reporter nucleic acid can comprise a fluorescent label, wherein the portion of the second reporter nucleic acid separated from the at least another portion of the second reporter nucleic acid comprises a fluorescent label, and wherein determining step (e) comprises detecting the fluorescent label. Determining step (e) can comprise detecting the portion of the first reporter nucleic acid separated from the at least another portion of the first reporter nucleic acid using a capillary electrophoresis technique. Determining step (e) can comprise detecting the portion of the second reporter nucleic acid separated from the at least another portion of the second reporter nucleic acid using a capillary electrophoresis technique. Steps (a), (b), (c), and (d) can be performed without nucleic acid amplification. Steps (a), (b), (c), (d), and (e) can be performed without nucleic acid amplification. The determining step can comprise determining the amount of the target nucleic acid present within the sample.

In another aspect, this document features a kit for assessing a sample for target nucleic acid. The kit comprises, or consists essentially of, a probe nucleic acid comprising an amplifying restriction endonuclease and a nucleotide sequence complementary to a sequence of the target nucleic acid, wherein at least a portion of the target nucleic acid is capable of hybridizing to at least a portion of the probe nucleic acid to form a double-stranded portion of nucleic acid comprising a restriction endonuclease cut site. The probe nucleic acid can be single-stranded probe nucleic acid. The kit can comprise a solid support, and the probe nucleic acid can be attached to the solid support. A portion of the probe nucleic acid comprising the amplifying restriction endonuclease can be releasable from the solid support via cleavage with a recognition restriction endonuclease having the ability to cleave at the restriction endonuclease cut site. The kit can further comprise the recognition restriction endonuclease. The probe nucleic acid can comprise (i) a single-stranded portion comprising the nucleotide sequence complementary to the sequence of the target nucleic acid and (ii) a double-stranded portion. The probe nucleic acid can comprise a first nucleic acid strand, which can comprise the nucleotide sequence complementary to the sequence of the target nucleic acid, hybridized to a second nucleic acid strand comprising the amplifying restriction endonuclease. The kit can further comprise a reporter nucleic acid comprising a double-stranded portion of nucleic acid comprising a restriction endonuclease cut site of the amplifying restriction endonuclease. The kit can comprise a solid support, and the reporter nucleic acid can be attached to the solid support. The reporter nucleic acid can be directly attached to the solid support. The reporter nucleic acid can comprise a single-stranded portion of nucleic acid. The reporter nucleic acid can comprise a label. The label can be a fluorescent label, a radioactive label, an enzyme label, or a redox label. A portion of the reporter nucleic acid comprising the label can be capable of being separated from at least another portion of the reporter nucleic acid via cleavage by the amplifying restriction endonuclease. The reporter nucleic acid can comprise a first nucleic acid strand, which can comprise the label, hybridized to a second nucleic acid strand. The kit can further comprise (a) a first signal expansion nucleic acid comprising a secondary amplifying restriction endonuclease and a double-stranded section having a restriction endonuclease cut site for the amplifying restriction endonuclease, and (b) a second signal expansion nucleic acid comprising the amplifying restriction endonuclease and a double-stranded section having a restriction endonuclease cut site for the secondary amplifying restriction endonuclease.

In another aspect, this document features a composition comprising, or consisting essentially of, nucleic acid covalently attached to a restriction endonuclease having the ability to cleave a double-stranded DNA molecule. The nucleic acid can comprise a single-stranded section having the ability to hybridize to target nucleic acid.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is a schematic depicting an exemplary method for detecting target nucleic acid using probe nucleic acid, a recognition restriction endonuclease, and reporter nucleic acid.

FIG. 4 is a schematic of an exemplary configuration of first signal expansion nucleic acid and second signal expansion nucleic acid that can be used with the methods and materials provided herein for detecting target nucleic acid. Such first signal expansion nucleic acid and second signal expansion nucleic acid can be used with or without reporter nucleic acid. When used without a separate reporter nucleic acid step, such signal expansion nucleic acid can be referred to as reporter nucleic acid.

FIG. 5 is a schematic of an exemplary configuration of first signal expansion nucleic acid and second signal expansion nucleic acid that can be used with the methods and materials provided herein for detecting target nucleic acid. Such first signal expansion nucleic acid and second signal expansion nucleic acid can be used with or without reporter nucleic acid. When used without a separate reporter nucleic acid step, such signal expansion nucleic acid can be referred to as reporter nucleic acid.

DETAILED DESCRIPTION

Figure 2:
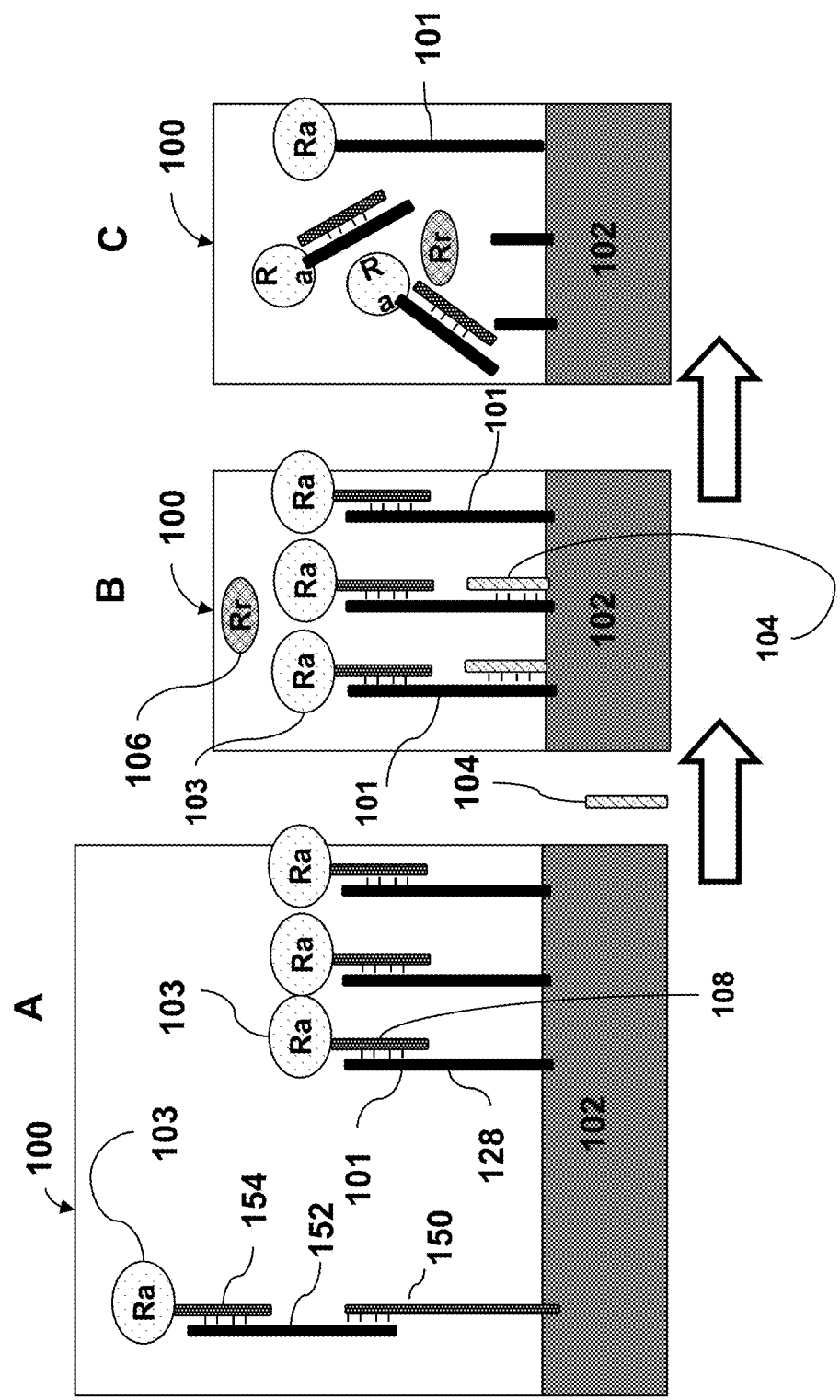
FIG. 2 is a schematic of an exemplary configuration of probe nucleic acid that can be used with the methods and materials provided herein for detecting target nucleic acid.

This document provides methods and materials for detecting target nucleic acid. For example, this document provides methods and materials for detecting the presence or absence of target nucleic acid within a sample, methods and materials for detecting the amount of target nucleic acid present within a sample, kits for detecting the presence or absence of target nucleic acid within a sample, kits for detecting the amount of target nucleic acid present within a sample, and methods for making such kits.

In one embodiment, a method for detecting target nucleic acid can include contacting a sample (e.g., a sample to be tested or suspected to contain target nucleic acid) with probe nucleic acid. The probe nucleic acid can be designed to have a single-stranded portion with a nucleotide sequence that is complementary to at least a portion of the target nucleic acid to be detected. In this case, target nucleic acid present within the sample can hybridize with the complementary sequence of this single-stranded portion of the probe nucleic acid to form a double-stranded section with one strand being target nucleic acid and the other strand being probe nucleic acid. In addition, the single-stranded portion of the probe nucleic acid having the nucleotide sequence that is complementary to at least a portion of the target nucleic acid to be detected can be designed such that hybridization with the target nucleic acid creates a restriction endonuclease cut site. Thus, target nucleic acid present within the sample can hybridize with the complementary sequence of the single-stranded portion of the probe nucleic acid to form a double-stranded section that creates a cut site for a restriction endonuclease. This cut site created by the hybridization of target nucleic acid to probe nucleic acid can be referred to as a recognition restriction endonuclease cut site. In addition, a restriction endonuclease that cleaves nucleic acid at such a recognition restriction endonuclease cut site can be referred to as a recognition restriction endonuclease.

The probe nucleic acid also can be designed to contain a restriction endonuclease. This restriction endonuclease, which can be a component of the probe nucleic acid, can be referred to as an amplifying restriction endonuclease. An amplifying restriction endonuclease is typically a different restriction endonuclease than the restriction endonuclease that is used as a recognition restriction endonuclease. For example, when an EcoRI restriction endonuclease is used as a recognition restriction endonuclease, a restriction endonuclease other than an EcoRI restriction endonuclease (e.g., a Hind III restriction endonuclease) is used as an amplifying restriction endonuclease. Thus, in general, probe nucleic acid is designed to contain an amplifying restriction endonuclease and to have a nucleotide sequence such that the target nucleic acid can hybridize to the probe nucleic acid and create a recognition restriction endonuclease cut site for a recognition restriction endonuclease. In some cases, the probe nucleic acid can be attached to a solid support (e.g., a well of a microtiter plate). For example, the probe nucleic acid can be attached to a solid support such that cleavage at the recognition restriction endonuclease cut site via the recognition restriction endonuclease releases a portion of the probe nucleic acid that contains the amplifying restriction endonuclease.

After contacting the sample that may or may not contain target nucleic acid with the probe nucleic acid that is attached to a solid support, the target nucleic acid, if present in the sample, can hybridize to the probe nucleic acid and create the recognition restriction endonuclease cut site. At this point, the recognition restriction endonuclease, whether added to the reaction or already present in the reaction, can cleave the probe nucleic acid at the recognition restriction endonuclease cut sites that are formed by the hybridization of target nucleic acid to the probe nucleic acid, thereby releasing the portion of the probe nucleic acid that contains the amplifying restriction endonuclease from the solid support. The number of amplifying restriction endonuclease-containing portions of the probe nucleic acid that are released from the solid support can be in an essentially linear relationship (e.g., essentially a one-for-one relationship) with the number of target nucleic acid molecules that hybridize with the probe nucleic acid to form the recognition restriction endonuclease cut site.

The portions of the probe nucleic acid containing the amplifying restriction endonuclease that were released from the solid support can be collected and placed in contact with reporter nucleic acid. For example, the released portions of the probe nucleic acid, if present, can be transferred from one well of a microtiter plate (e.g., a 96-well plate) that contained the probe nucleic acid to another well of a microtiter plate that contains the reporter nucleic acid. The reporter nucleic acid can be designed to have a double-stranded portion with a restriction endonuclease cut site for the amplifying restriction endonuclease of the probe nucleic acid. This restriction endonuclease cut site for the amplifying restriction endonuclease can be referred to as an amplifying restriction endonuclease cut site. If portions of the probe nucleic acid containing the amplifying restriction endonuclease are present and placed in contact with the reporter nucleic acid, then the reporter nucleic acid can be cleaved at the amplifying restriction endonuclease cut site by the amplifying restriction endonuclease. Since the amplifying restriction endonucleases of the released portions of the probe nucleic acid are free to carry out repeated cleavage events, the number of reporter nucleic acid molecules that are cleaved can greatly exceed the number of amplifying restriction endonucleases present in the reaction. For example, the number of cleaved reporter nucleic acid molecules can greatly exceed (e.g., exponentially exceed) the number of amplifying restriction endonucleases present in the reaction and therefore can greatly exceed (e.g., exponentially exceed) the number of target nucleic acid molecules that were present in the sample contacted with the probe nucleic acid. Such a greatly expanded relationship (e.g., an exponential relationship) can allow very small amounts of target nucleic acid present in the sample to be readily detected.

After the released portions of the probe nucleic acid, if present, are contacted with the reporter nucleic acid, the presence or absence of cleaved reporter nucleic acid can be determined. The presence of cleaved reporter nucleic acid can indicate that the sample contained the target nucleic acid, while the absence of cleaved reporter nucleic acid can indicate that the sample lacked the target nucleic acid. In some cases, the amount of cleaved reporter nucleic acid can be determined. In such cases, the amount of cleaved reporter nucleic acid can indicate the amount of target nucleic acid present in the sample. A standard curve using known amounts of target nucleic acid can be used to aid in the determination of the amount of target nucleic acid present within a sample.

In some cases, the reporter nucleic acid can contain a label to aid in the detection of cleaved reporter nucleic acid. For example, reporter nucleic acid can contain a fluorescent label and a quencher such that cleaved reporter nucleic acid provides a fluorescent signal and uncleaved reporter nucleic acid does not provide a fluorescent signal. In some cases, the reporter nucleic acid can contain a label (e.g., a colorimetric label, a fluorescent label or an enzyme such as horse radish peroxidase) and can be attached to a solid support (e.g., a well of a microtiter plate). For example, the reporter nucleic acid can be attached to a solid support such that cleavage at the amplifying restriction endonuclease cut site by the amplifying restriction endonuclease releases a portion of the reporter nucleic acid that contains the label. The resulting reaction mixture can be collected and assessed for the presence, absence, or amount of released portions of the reporter nucleic acid using the label. For example, the released portions of the reporter nucleic acid, if present, can be transferred from one well of a microtiter plate (e.g., a 96-well plate) that contained the reporter nucleic acid to another well of a microtiter plate, where the transferred material can be assessed for a signal from the label.

One example of a method of detecting target nucleic acid that includes using probe nucleic acid and reporter nucleic acid is set forth in FIG. 1. With reference to FIG. 1, first reaction chamber 100 (e.g., a microtiter plate well) can contain probe nucleic acid 101. Probe nucleic acid 101 can be attached (e.g., immobilized) to solid support 102 and can include amplifying restriction endonuclease 103 (Ra). Probe nucleic acid 101 can be attached to solid support 102 such that amplifying restriction endonuclease 103 is released from solid support 102 upon cleavage of a nucleic acid component of probe nucleic acid 101. Probe nucleic acid 101 can have a single-stranded section having a nucleotide sequence that is complementary to at least a portion of target nucleic acid 104. Probe nucleic acid 101 can be contacted with a sample that may or may not contain target nucleic acid 104. If target nucleic acid 104 is present, at least a portion of target nucleic acid 104 and probe nucleic acid 101 can hybridize to form a double-stranded section of nucleic acid. Such a double-stranded section can contain at least one recognition restriction endonuclease cut site 105. Addition of recognition restriction endonuclease 106 (Rr) to first reaction chamber 100 can result in the cleave of probe nucleic acid 101 at recognition restriction endonuclease cut site 105 formed by one strand of probe nucleic acid and one strand of target nucleic acid, thereby releasing portion 107 of probe nucleic acid 101 from solid support 102. Portion 107 can include amplifying restriction endonuclease 103.

The reaction product from first reaction chamber 100 containing released portion 107, if target nucleic acid 104 was present, can be transferred (e.g., manually or automatically) to second reaction chamber 120. Second reaction chamber 120 can contain reporter nucleic acid 121. Reporter nucleic acid 121 can be attached (e.g., immobilized) to solid support 122 and can include marker (e.g., a label) 123 (M). Reporter nucleic acid 121 can be attached to solid support 122 such that marker 123 is released from solid support 122 upon cleavage of a nucleic acid component of reporter nucleic acid 121. Reporter nucleic acid 121 can have at least one double-stranded portion that contains at least one amplifying restriction endonuclease cut site 124. Addition of the reaction product from first reaction chamber 100 to second reaction chamber 120 can result in the cleavage of reporter nucleic acid 121 at amplifying restriction endonuclease cut site 124 if the reaction product contains portion 107. Such cleavage of reporter nucleic acid 121 can result in the release of portion 127 from solid support 122. Portion 127 can include marker 123.

The reaction product from second reaction chamber 120 can be assessed to determine the presence, absence, or amount of portion 127. The presence of portion 127 can indicate that the sample contained target nucleic acid 104, while the absence of portion 127 can indicate that the sample lacked target nucleic acid 104. In some cases, the amount of portion 127 can be determined. In such cases, the amount of portion 127 can indicate the amount of target nucleic acid 104 present in the sample. The presence, absence, or amount of portion 127 can be determined using marker 123, and portion 127 having marker 123 can be distinguished from uncleaved reporter nucleic acid 121 having marker 123 since, in this example, portion 127 is released from solid support 122, while uncleaved reporter nucleic acid 121 remains attached to solid support 122. For example, in some cases, the reaction product from second reaction chamber 120 can be transferred to third reaction chamber where the presence or absence of portion 127 via marker 123 is assessed. If portion 127 is present, the amount of portion 127 present can be quantified.

Probe nucleic acid 101 and reporter nucleic acid 121 can have various configurations. For example, with reference to FIG. 1, probe nucleic acid 101 can be designed to have a single nucleic acid strand such that the entire nucleic acid component of probe nucleic acid 101 is single-stranded prior to contact with target nucleic acid 104. In another example, with reference to FIG. 2, probe nucleic acid 101 can be designed to have first strand 128 and second strand 108. First strand 128 can be attached to solid support 102 and can be designed to have a single-stranded section having a nucleotide sequence that is complementary to at least a portion of target nucleic acid 104. Second strand 108 can include amplifying restriction endonuclease 103 and can have a single-stranded section having a nucleotide sequence that can hybridize to first strand 128. In some cases, first strand 128 and second strand 108 can be synthesized or obtained separately and then mixed together to form probe nucleic acid 101. For example, first strand 128 can be synthesized, biotinylated, and attached to a streptavidin-coated solid support. After synthesizing the nucleic acid component of second strand 108 and attaching amplifying restriction endonuclease 103 to the synthesized nucleic acid component, second strand 108 can be incubated with first strand 128 to form nucleic acid probe 101. In some cases, probe nucleic acid 101 can contain more than two strands. For example, probe nucleic acid can include first strand 150, second strand 152, and third strand 154. In this case, first strand 150 can be attached to solid support 102, second strand 152 can be hybridized to first strand 150 and can include a single-stranded section having a nucleotide sequence that is complementary to at least a portion of target nucleic acid 104, and third strand 154 can be hybridized to second strand 152 and can be attached to amplifying restriction endonuclease 103. Similar one, two, three, or more strand configurations can be used to make reporter nucleic acid.

In another embodiment, a method for detecting target nucleic acid can include contacting a sample (e.g., a sample to be tested or suspected to contain target nucleic acid) with probe nucleic acid. The probe nucleic acid can be designed to have a single-stranded portion with a nucleotide sequence that is complementary to at least a portion of the target nucleic acid to be detected. In this case, target nucleic acid present within the sample can hybridize with the complementary sequence of this single-stranded portion of the probe nucleic acid to form a double-stranded section with one strand being target nucleic acid and the other strand being probe nucleic acid. In addition, the single-stranded portion of the probe nucleic acid having the nucleotide sequence that is complementary to at least a portion of the target nucleic acid to be detected can be designed such that hybridization with the target nucleic acid creates a recognition restriction endonuclease cut site. Thus, target nucleic acid present within the sample can hybridize with the complementary sequence of the single-stranded portion of the probe nucleic acid to form a double-stranded section that creates a recognition restriction endonuclease cut site for a recognition restriction endonuclease. The probe nucleic acid also can be designed to contain an amplifying restriction endonuclease. Since this method includes the use of two or more different amplifying restriction endonucleases, the amplifying restriction endonuclease that is a component of the probe nucleic acid can be referred to as a first or an initial amplifying restriction endonuclease, with additional amplifying restriction endonucleases being referred to as second, third, and so on or secondary, tertiary, and so on amplifying restriction endonucleases. This initial amplifying restriction endonuclease is typically a different restriction endonuclease than the restriction endonuclease that is used as a recognition restriction endonuclease. For example, when an EcoRI restriction endonuclease is used as a recognition restriction endonuclease, a restriction endonuclease other than an EcoRI restriction endonuclease (e.g., a Hind III restriction endonuclease) is used as an initial amplifying restriction endonuclease. Thus, in general, probe nucleic acid is designed to contain an initial amplifying restriction endonuclease and to have a nucleotide sequence such that the target nucleic acid can hybridize to the probe nucleic acid and create a recognition restriction endonuclease cut site for a recognition restriction endonuclease. In some cases, the probe nucleic acid can be attached to a solid support (e.g., a well of a microtiter plate). For example, the probe nucleic acid can be attached to a solid support such that cleavage at the recognition restriction endonuclease cut site via the recognition restriction endonuclease releases a portion of the probe nucleic acid that contains the initial amplifying restriction endonuclease.

After contacting the sample that may or may not contain target nucleic acid with the probe nucleic acid that is attached to a solid support, the target nucleic acid, if present in the sample, can hybridize to the probe nucleic acid and create the recognition restriction endonuclease cut site. At this point, the recognition restriction endonuclease, whether added to the reaction or already present in the reaction, can cleave the probe nucleic acid at the recognition restriction endonuclease cut sites that are formed by the hybridization of target nucleic acid to the probe nucleic acid, thereby releasing the portion of the probe nucleic acid that contains the initial amplifying restriction endonuclease from the solid support. The number of initial amplifying restriction endonuclease-containing portions of the probe nucleic acid that are released from the solid support can be in an essentially linear relationship (e.g., essentially a one-for-one relationship) with the number of target nucleic acid molecules that hybridize with the probe nucleic acid to form the recognition restriction endonuclease cut site.

The portions of the probe nucleic acid containing the initial amplifying restriction endonuclease that were released from the solid support can be collected and placed in contact with first signal expansion nucleic acid and second signal expansion nucleic acid. The first signal expansion nucleic acid can be designed to have a double-stranded portion with a restriction endonuclease cut site for the initial amplifying restriction endonuclease of the probe nucleic acid. This restriction endonuclease cut site for the initial amplifying restriction endonuclease can be referred to as an initial amplifying restriction endonuclease cut site. The first signal expansion nucleic acid also can be designed to contain a secondary amplifying restriction endonuclease. The second signal expansion nucleic acid can be designed to have a double-stranded portion with a restriction endonuclease cut site for the secondary amplifying restriction endonuclease of the first signal expansion nucleic acid. This restriction endonuclease cut site for the secondary amplifying restriction endonuclease can be referred to as a secondary amplifying restriction endonuclease cut site. The second signal expansion nucleic acid also can be designed to contain an initial amplifying restriction endonuclease. For example, when an EcoRI restriction endonuclease is used as a recognition restriction endonuclease and a HindIII restriction endonuclease is used as an initial amplifying restriction endonuclease of the probe nucleic acid, a SmaI restriction endonuclease can be used as a secondary amplifying restriction endonuclease of the first signal expansion nucleic acid and a HindIII restriction endonuclease can be used as the initial amplifying restriction endonuclease of the second signal expansion nucleic acid.

In some cases, the first signal expansion nucleic acid and second signal expansion nucleic acid can be attached to a solid support (e.g., a well of a microtiter plate). For example, the first signal expansion nucleic acid can be attached to a solid support such that cleavage at the initial amplifying restriction endonuclease cut site via the initial amplifying restriction endonuclease releases a portion of the first signal expansion nucleic acid that contains the secondary amplifying restriction endonuclease, and the second signal expansion nucleic acid can be attached to a solid support such that cleavage at the secondary amplifying restriction endonuclease cut site via the secondary amplifying restriction endonuclease releases a portion of the second signal expansion nucleic acid that contains the initial amplifying restriction endonuclease. The first signal expansion nucleic acid can be attached to the same solid support (e.g., two different sub-compartments of a larger compartment) that contains the second signal expansion nucleic acid provided that the secondary amplifying restriction endonuclease of uncleaved first signal expansion nucleic acid is unable to cleave the second signal expansion nucleic acid and provided that the initial amplifying restriction endonuclease of uncleaved second signal expansion nucleic acid is unable to cleave the first signal expansion nucleic acid. In some cases, the first signal expansion nucleic acid can be attached to the same solid support within a joint compartment such that the first signal expansion nucleic acid is within a first compartment of the joint compartment and the second signal expansion nucleic acid is within a second compartment of the joint compartment. In such cases, the secondary amplifying restriction endonuclease of uncleaved first signal expansion nucleic acid in the first compartment is unable to cleave the second signal expansion nucleic acid located in the second compartment, while the secondary amplifying restriction endonuclease of cleaved first signal expansion nucleic acid is capable of moving (e.g., diffusing) from the first compartment to the second compartment to cleave the second signal expansion nucleic acid located in the second compartment. In addition, the initial amplifying restriction endonuclease of uncleaved second signal expansion nucleic acid in the second compartment is unable to cleave the first signal expansion nucleic acid located in the first compartment, while the initial amplifying restriction endonuclease of cleaved second signal expansion nucleic acid is capable of moving (e.g., diffusing) from the second compartment to the first compartment to cleave the first signal expansion nucleic acid located in the first compartment.

If portions of the probe nucleic acid containing the initial amplifying restriction endonuclease are present and placed in contact with the first signal expansion nucleic acid, then the first signal expansion nucleic acid can be cleaved at the initial amplifying restriction endonuclease cut site by the initial amplifying restriction endonuclease, thereby releasing a portion of the first signal expansion nucleic acid that contains the secondary amplifying restriction endonuclease from the solid support. The released portions of the first signal expansion nucleic acid containing the secondary amplifying restriction endonuclease can be free to cleave the second signal expansion nucleic acid at the secondary amplifying restriction endonuclease cut site, thereby releasing a portion of the second signal expansion nucleic acid that contains the initial amplifying restriction endonuclease from the solid support. Since the initial amplifying restriction endonucleases of the released portions of the probe nucleic acid, the initial amplifying restriction endonucleases of the released portions of the second signal expansion nucleic acid, and the secondary amplifying restriction endonucleases of the released portions of the first signal expansion nucleic acid are free to carry out repeated cleavage events, the number of released portions containing the initial amplifying restriction endonucleases is greatly increased from the number that were released by the recognition restriction endonuclease. For example, the number of cleaved first signal expansion nucleic acid molecules can greatly exceed (e.g., exponentially exceed) the number of released portions of the probe nucleic acid, and the number of cleaved second signal expansion nucleic acid molecules can greatly exceed (e.g., exponentially exceed) the number of released portions of the probe nucleic acid. Such a greatly expanded relationship (e.g., an exponential relationship) can allow very small amounts of target nucleic acid present in the sample to be readily detected.

In some cases, this method can be performed with the first signal expansion nucleic acid being attached to a solid support that is different from the solid support that contains the second signal expansion nucleic acid. For example, the first signal expansion nucleic acid can be attached to one well of a microtiter plate, while the second signal expansion nucleic acid can be attached to a different well of a microtiter plate. In this case, the resulting reaction material from the well with the first signal expansion nucleic acid can be collected and transferred to the well containing the second signal expansion nucleic acid.

The portions of the second signal expansion nucleic acid containing the initial amplifying restriction endonuclease that were released from the solid support containing the second signal expansion nucleic acid along with any other released portions in this reaction (e.g., the released portions of the probe nucleic acid containing the initial amplifying restriction endonuclease and the released portions of the first signal expansion nucleic acid containing the secondary amplifying restriction endonuclease) can be collected and placed in contact with reporter nucleic acid. For example, the released portions, if present, can be transferred from one well of a microtiter plate (e.g., a 96-well plate) that contained the second signal expansion nucleic acid to another well of a microtiter plate that contains the reporter nucleic acid. The reporter nucleic acid can be designed to have a double-stranded portion with a restriction endonuclease cut site for the initial amplifying restriction endonuclease. If released portions containing the initial amplifying restriction endonuclease are present and placed in contact with the reporter nucleic acid, then the reporter nucleic acid can be cleaved at the initial amplifying restriction endonuclease cut site by the initial amplifying restriction endonuclease. Since the initial amplifying restriction endonucleases of the released portions are free to carry out repeated cleavage events, the number of reporter nucleic acid molecules that are cleaved can greatly exceed the number of initial amplifying restriction endonucleases present in the reaction. For example, the number of cleaved reporter nucleic acid molecules can greatly exceed (e.g., exponentially exceed) the number of initial amplifying restriction endonucleases present in the reaction and therefore can greatly exceed (e.g., exponentially exceed) the number of target nucleic acid molecules that were present in the sample contacted with the probe nucleic acid. Such a greatly expanded relationship (e.g., an exponential relationship) can allow very small amounts of target nucleic acid present in the sample to be readily detected.

After the released portions containing the initial amplifying restriction endonuclease, if present, are contacted with the reporter nucleic acid, the presence or absence of cleaved reporter nucleic acid can be determined. The presence of cleaved reporter nucleic acid can indicate that the sample contained the target nucleic acid, while the absence of cleaved reporter nucleic acid can indicate that the sample lacked the target nucleic acid. In some cases, the amount of cleaved reporter nucleic acid can be determined. In such cases, the amount of cleaved reporter nucleic acid can indicate the amount of target nucleic acid present in the sample.

In some cases, the reporter nucleic acid can contain a label to aid in the detection of cleaved reporter nucleic acid. For example, reporter nucleic acid can contain a fluorescent label and a quencher such that cleaved reporter nucleic acid provides a fluorescent signal and uncleaved reporter nucleic acid does not provide a fluorescent signal. In some cases, the reporter nucleic acid can contain a label (e.g., a colorimetric label, fluorescent label or an enzyme such as horse radish peroxidase) and can be attached to a solid support (e.g., a well of a microtiter plate). For example, the reporter nucleic acid can be attached to a solid support such that cleavage at the initial amplifying restriction endonuclease cut site by the initial amplifying restriction endonuclease releases a portion of the reporter nucleic acid that contains the label. The resulting reaction mixture can be collected and assessed for the presence, absence, or amount of released portions of the reporter nucleic acid using the label. For example, the released portions of the reporter nucleic acid, if present, can be transferred from one well of a microtiter plate (e.g., a 96-well plate) that contained the reporter nucleic acid to another well of a microtiter plate, where the transferred material can be assessed for a signal from the label.

In some cases, the presence or absence of cleaved first signal expansion nucleic acid, cleaved second signal expansion nucleic acid, or both can be determined. The presence of such cleaved nucleic acid can indicate that the sample contained the target nucleic acid, while the absence of such cleaved nucleic acid can indicate that the sample lacked the target nucleic acid. In some cases, the amount of cleaved first signal expansion nucleic acid, cleaved second signal expansion nucleic acid, or both can be determined. In such cases, the amount of cleaved nucleic acid can indicate the amount of target nucleic acid present in the sample. In these cases, the use of cleaved first signal expansion nucleic acid, cleaved second signal expansion nucleic acid, or both to assess the sample for target nucleic acid can be in addition to the use of a separate reporter nucleic acid step or can replace the use of a separate reporter nucleic acid step. In some cases, the first signal expansion nucleic acid, the second signal expansion nucleic acid, or both can be labeled in a manner similar to that described herein for the reporter nucleic acid to aid in detection. When the presence, absence, or amount of cleaved first signal expansion nucleic acid, cleaved second signal expansion nucleic acid, or both are determined to assess the sample for target nucleic acid, the first signal expansion nucleic acid can be referred to as a first reporter nucleic acid and the second signal expansion nucleic acid can be referred to as a second reporter nucleic acid even though they include amplifying restriction endonucleases.

Figure 3:
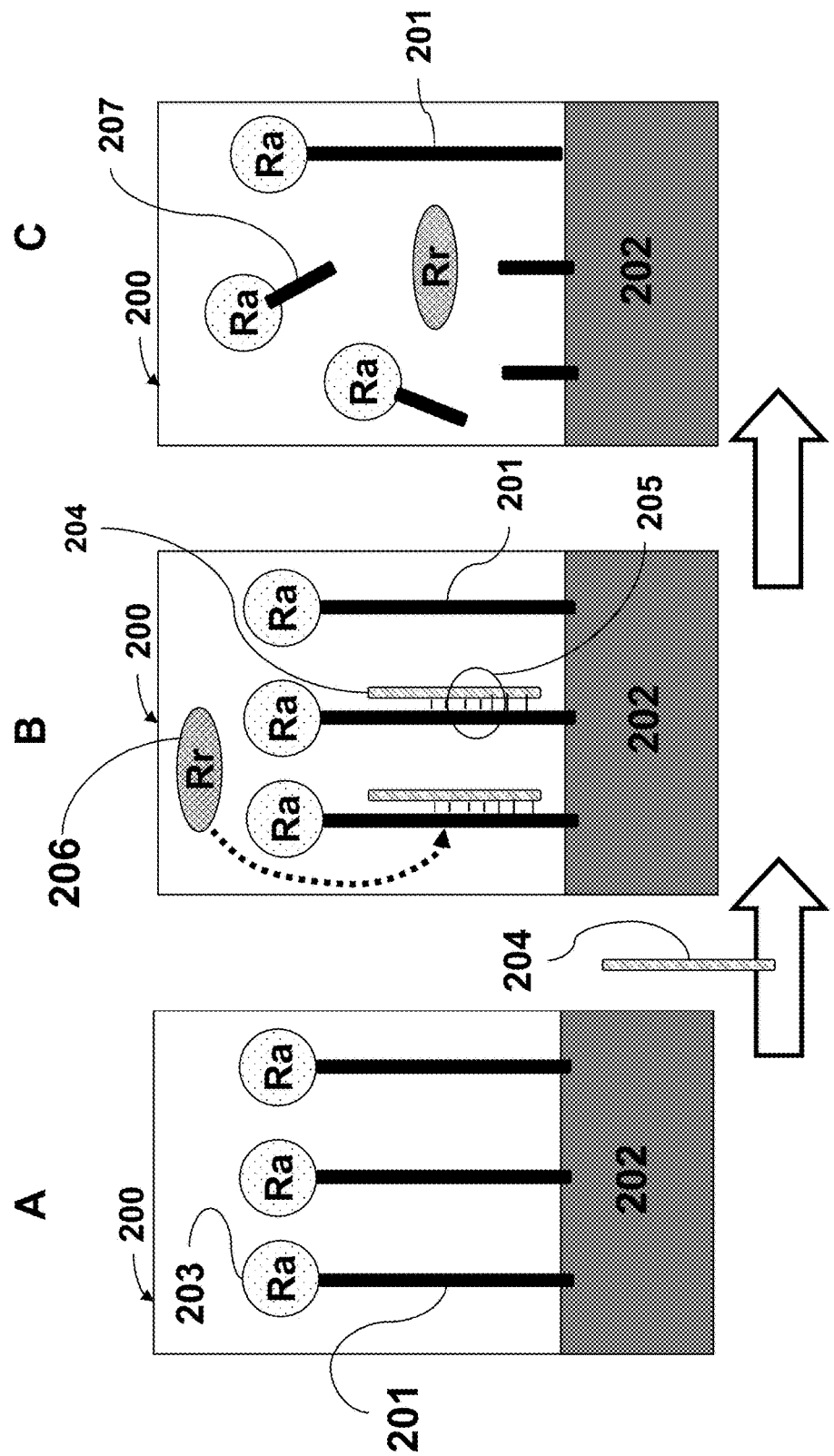
FIG. 3 is a schematic depicting an exemplary method for detecting target nucleic acid using probe nucleic acid, a recognition restriction endonuclease, first signal expansion nucleic acid, second signal expansion nucleic acid, and reporter nucleic acid.

Examples of a method of detecting target nucleic acid that includes using probe nucleic acid, first signal expansion nucleic acid, second signal expansion nucleic acid, and reporter nucleic acid are set forth in FIGS. 3-5. With reference to FIG. 3, first reaction chamber 200 (e.g., a microtiter plate well) can contain probe nucleic acid 201. Probe nucleic acid 201 can be attached (e.g., immobilized) to solid support 202 and can include initial amplifying restriction endonuclease 203 (Ra). Probe nucleic acid 201 can be attached to solid support 202 such that initial amplifying restriction endonuclease 203 is released from solid support 202 upon cleavage of a nucleic acid component of probe nucleic acid 201. Probe nucleic acid 201 can have a single-stranded section having a nucleotide sequence that is complementary to at least a portion of target nucleic acid 204. Probe nucleic acid 201 can be contacted with a sample that may or may not contain target nucleic acid 204. If target nucleic acid 204 is present, at least a portion of target nucleic acid 204 and probe nucleic acid 201 can hybridize to form a double-stranded section of nucleic acid. Such a double-stranded section can contain at least one recognition restriction endonuclease cut site 205. Addition of recognition restriction endonuclease 206 (Rr) to first reaction chamber 200 can result in the cleavage of probe nucleic acid 201 at recognition restriction endonuclease cut site 205 formed by one strand of probe nucleic acid and one strand of target nucleic acid, thereby releasing portion 207 of probe nucleic acid 201 from solid support 202. Portion 207 can include initial amplifying restriction endonuclease 203.

The reaction product from first reaction chamber 200 containing released portion 207, if target nucleic acid 204 was present, can be transferred (e.g., manually or automatically) to second reaction chamber 220. Second reaction chamber 220 can contain first signal expansion nucleic acid 226 and second signal expansion nucleic acid 225. First signal expansion nucleic acid 226 can have at least one double-stranded portion that contains at least one initial amplifying restriction endonuclease cut site 230. First signal expansion nucleic acid 226 can be attached (e.g., immobilized) to solid support 222 and can include secondary amplifying restriction endonuclease 223 (Rb). First signal expansion nucleic acid 226 can be attached to solid support 222 such that portion 234 containing secondary amplifying restriction endonuclease 223 is released from solid support 222 upon cleavage of first signal expansion nucleic acid 226 at initial amplifying restriction endonuclease cut site 230. For clarity, frame E of FIG. 3 omits depicting one strand from the cleaved versions of first signal expansion nucleic acid 226 and second signal expansion nucleic acid 225.

Second signal expansion nucleic acid 225 can have at least one double-stranded portion that contains at least one secondary amplifying restriction endonuclease cut site 232. Second signal expansion nucleic acid 225 can be attached (e.g., immobilized) to solid support 222 and can include initial amplifying restriction endonuclease 224. Second signal expansion nucleic acid 225 can be attached to solid support 222 such that portion 236 containing initial amplifying restriction endonuclease 224 is released from solid support 222 upon cleavage of second signal expansion nucleic acid 225 at secondary amplifying restriction endonuclease cut site 232. Initial amplifying restriction endonuclease 203 of probe nucleic acid 201 and initial amplifying restriction endonuclease 224 of second signal expansion nucleic acid 225 can be the same restriction endonuclease. For example, both can be an EcoRI restriction endonuclease.

Addition of the reaction product from first reaction chamber 200 to second reaction chamber 220 can result in the cleavage of first signal expansion nucleic acid 226 at initial amplifying restriction endonuclease cut site 230 if the reaction product contains portion 207. Such cleavage of first signal expansion nucleic acid 226 can result in the release of portion 234 from solid support 222. Portion 234, which can include secondary amplifying restriction endonuclease 223, can result in the cleavage of second signal expansion nucleic acid 225 at secondary amplifying restriction endonuclease cut site 232. Such cleavage of second signal expansion nucleic acid 225 can result in the release of portion 236 from solid support 222. Thus, this reaction can result in the accumulation of released portions 234 and 236.

The reaction product from second reaction chamber 220 containing released portion 207, released portion 234, and released portion 236, if target nucleic acid 204 was present, can be transferred (e.g., manually or automatically) to third reaction chamber 240. Third reaction chamber 240 can contain reporter nucleic acid 241. Reporter nucleic acid 241 can be attached (e.g., immobilized) to solid support 242 and can include marker (e.g., a label) 243 (M). Reporter nucleic acid 241 can be attached to solid support 242 such that marker 243 is released from solid support 242 upon cleavage of a nucleic acid component of reporter nucleic acid 241. Reporter nucleic acid 241 can have at least one double-stranded portion that contains at least one initial amplifying restriction endonuclease cut site 246. Addition of the reaction product from second reaction chamber 220 to third reaction chamber 240 can result in the cleavage of reporter nucleic acid 241 at initial amplifying restriction endonuclease cut site 246 if the reaction product contains portion 207 and portion 236. In some cases, reporter nucleic acid 241 can include at least one double-stranded portion that contains at least one cut site for secondary amplifying restriction endonuclease 223. In such cases, addition of the reaction product from second reaction chamber 220 to third reaction chamber 240 can result in the cleavage of reporter nucleic acid 241 at the cut site for secondary amplifying restriction endonuclease 223 if the reaction product contains portion 234. Cleavage of reporter nucleic acid 241 can result in the release of portion 247 from solid support 242. Portion 247 can include marker 243.

The reaction product from third reaction chamber 240 can be assessed to determine the presence, absence, or amount of portion 247. The presence of portion 247 can indicate that the sample contained target nucleic acid 204, while the absence of portion 247 can indicate that the sample lacked target nucleic acid 204. In some cases, the amount of portion 247 can be determined. In such cases, the amount of portion 247 can indicate the amount of target nucleic acid 204 present in the sample. The presence, absence, or amount of portion 247 can be determined using marker 243, and portion 247 having marker 243 can be distinguished from uncleaved reporter nucleic acid 241 having marker 243 since, in this example, portion 247 is released from solid support 242, while uncleaved reporter nucleic acid 241 remains attached to solid support 242. For example, in some cases, the reaction product from third reaction chamber 24 can be transferred to fourth reaction chamber where the presence or absence of portion 247 via marker 243 is assessed. If portion 347 is present, the amount of portion 247 present can be quantified.

In some cases and with reference to FIGS. 4 and 5, first signal expansion nucleic acid 226 can include marker (e.g., a label) 243 (M) and second signal expansion nucleic acid 225 can include marker (e.g., a label) 243 (M). In such cases, cleavage of first signal expansion nucleic acid 226 and cleavage of second signal expansion nucleic acid 225 can be assessed using marker 243 to determine the presence, absence, or amount of target nucleic acid within a sample. For example, detector 250 can be used to detect marker 243 released from solid support 222.

Probe nucleic acid 201, first signal expansion nucleic acid 226, second signal expansion nucleic acid 225, and reporter nucleic acid 241 can have various configurations. For example, with reference to FIG. 3, probe nucleic acid 201 can be designed to have a single nucleic acid strand such that the entire nucleic acid component of probe nucleic acid 201 is single-stranded prior to contact with target nucleic acid 204. In another example, probe nucleic acid 201 can be designed in a manner like probe nucleic acid 101 to have two or more strands. See, e.g., FIG. 2. For example, probe nucleic acid 201 can have a first strand and a second strand. The first strand can be attached to a solid support and can be designed to have a single-stranded section having a nucleotide sequence that is complementary to at least a portion of target nucleic acid. The second strand can include an initial amplifying restriction endonuclease and can have a single-stranded section having a nucleotide sequence that can hybridize to the first strand. In some cases, the first strand and second strand can be synthesized or obtained separately and then mixed together to form probe nucleic acid 201. For example, the first strand can be synthesized, biotinylated, and attached to a streptavidin-coated solid support. After synthesizing the nucleic acid component of the second strand and attaching an initial amplifying restriction endonuclease to the synthesized nucleic acid component, the second strand can be incubated with the first strand to form nucleic acid probe 201. In some cases, probe nucleic acid 201 can contain more than two strands. For example, probe nucleic acid can include a first strand, a second strand, and a third strand. In this case, the first strand can be attached to a solid support, the second strand can be hybridized to the first strand and can include a single-stranded section having a nucleotide sequence that is complementary to at least a portion of target nucleic acid, and the third strand can be hybridized to the second strand and can be attached to an initial amplifying restriction endonuclease. Similar one, two, three, or more strand configurations can be used to make first signal expansion nucleic acid, second signal expansion nucleic acid, or reporter nucleic acid. For example, first signal expansion nucleic acid and second signal expansion nucleic acid can be designed to have a configuration as shown in FIG. 4 or 5.

Probe nucleic acid described herein typically includes at least one single-stranded DNA section that is designed to hybridize with a desired target nucleic acid and thereby create a recognition restriction endonuclease cut site. The other portions of the probe nucleic acid can include DNA, RNA, or other molecules. For example, probe nucleic acid can include biotin such that the probe nucleic acid can be attached to a streptavidin-coated solid support. In some cases, the single-stranded section of the probe nucleic acid that is designed to hybridize with a desired target nucleic acid and create a recognition restriction endonuclease cut site can be RNA or a nucleic acid analog (e.g., a peptide nucleic acid (PNA)) provided that such a single-stranded section can (i) hybridize with the desired target nucleic acid and (ii) create a recognition restriction endonuclease cut site with the complementary target nucleic acid sequence that is capable of being cleaved by the recognition restriction endonuclease. Examples of restriction endonucleases that can be used as recognition restriction endonucleases to cleave a recognition restriction endonuclease cut site that is created between an RNA section of the probe nucleic acid and a DNA section of the target nucleic acid include, without limitation, HhaI, AluI, TaqI, HaeIII, EcoRI, HindII, SalI, and MspI restriction endonucleases.

Probe nucleic acid described herein can be any length provided that the single-stranded section of the probe nucleic acid that is designed to hybridize with a desired target nucleic acid is capable of hybridizing to the target nucleic acid and provided that the amplifying restriction endonuclease of the probe nucleic acid is capable of cleaving its amplifying restriction endonuclease cut site after the probe nucleic acid is cleaved by a recognition restriction endonuclease. In general, the single-stranded section of the probe nucleic acid that is designed to hybridize with a desired target nucleic acid can be between about 10 and about 500 or more nucleotides (e.g., between about 10 and about 400 nucleotides, between about 10 and about 300 nucleotides, between about 10 and about 200 nucleotides, between about 10 and about 100 nucleotides, between about 10 and about 50 nucleotides, between about 10 and about 25 nucleotides, between about 20 and about 500 nucleotides, between about 30 and about 500 nucleotides, between about 40 and about 500 nucleotides, between about 50 and about 500 nucleotides, between about 15 and about 50 nucleotides, between about 15 and about 25 nucleotides, between about 20 and about 50 nucleotides, or between about 18 and about 25 nucleotides) in length. The recognition restriction endonuclease cut site that will be created by the hybridization of target nucleic acid to this single-stranded section of the probe nucleic acid can be located at any position alone the single-stranded section. For example, the recognition restriction endonuclease cut site to be created can be towards the 5' end, towards the '3 end, or near the center of the single-stranded section of the probe nucleic acid. In general, the overall length of the probe nucleic acid described herein can be between about 10 and about 2500 or more nucleotides (e.g., between about 10 and about 2000 nucleotides, between about 10 and about 1000 nucleotides, between about 10 and about 500 nucleotides, between about 10 and about 400 nucleotides, between about 10 and about 300 nucleotides, between about 10 and about 200 nucleotides, between about 10 and about 100 nucleotides, between about 10 and about 50 nucleotides, between about 10 and about 25 nucleotides, between about 20 and about 500 nucleotides, between about 30 and about 500 nucleotides, between about 40 and about 500 nucleotides, between about 50 and about 500 nucleotides, between about 75 and about 500 nucleotides, between about 100 and about 500 nucleotides, between about 150 and about 500 nucleotides, between about 15 and about 50 nucleotides, between about 15 and about 25 nucleotides, between about 20 and about 50 nucleotides, or between about 18 and about 25 nucleotides) in length.

The recognition restriction endonuclease cut site to be created by hybridization of target nucleic acid to the probe nucleic acid can be a cut site of any type of restriction endonuclease. In addition, any type of restriction endonuclease can be used as a recognition restriction endonuclease to cleave probe nucleic acid upon target nucleic acid hybridization. Examples of restriction endonucleases that can be used as recognition restriction endonucleases include, without limitation, EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SphI, StuI, XbaI, AarI, BanII, BseGI, BspPI, CfrI, EcoNI, Hsp92II, NlaIV, RsaI, TaiI, AasI, BbsI, BseJI, BspTI, ClaI, EcoO109I, I-PpoI, NmuCI, RsrII, TaqaI, AatII, BbuI, BseLI, BsrBI, CpoI, KasI, Acc65I, BbvCI, BseMI, BsrDI, Csp45I, Kpn2I, NruI, SacII, TasI, AccB7I, BbvI, BseMII, BsrFI, Csp6I, EheI, KpnI, NsbI, SalI, TatI, AccI, BceAI, BseNI, BsrGI, CspI, Esp3I, KspAI, NsiI, SapI, and TauI restriction endonucleases. In some cases, nucleic acid encoding a naturally-occurring restriction endonuclease can be genetically engineered to create a modified restriction endonuclease that has the ability to recognize a particular cut site. Common computer algorithms can be used to locate restriction endonuclease cut sites along the nucleotide sequence of any desired target nucleic acid. Once located, the sequence of the restriction endonuclease cut site along with additional flanking sequence (e.g., 5' flanking sequence, 3' flanking sequence, or both 5' and 3' flanking sequence) can be used to design the complementary sequence of the probe nucleic acid that is used to hybridize to the target nucleic acid and create the recognition restriction endonuclease cut site upon target nucleic acid hybridization.

In general, probe nucleic acid can be designed to have a single-stranded section that is designed to hybridize with desired target nucleic acid and to form a single recognition restriction endonuclease cut site upon target nucleic acid hybridization. In some cases, probe nucleic acid can be designed to have a single-stranded section that is designed to hybridize with desired target nucleic acid and to form more than one (e.g., two, three, four, five, six, seven, eight, nine, ten, or more) recognition restriction endonuclease cut site upon target nucleic acid hybridization. When more than one recognition restriction endonuclease cut site is used, the multiple recognition restriction endonuclease cut sites can be cut sites for the same restriction endonuclease or cut sites for different restriction endonucleases. For example, probe nucleic acid can be designed to have a single-stranded section that is designed to hybridize with desired target nucleic acid and to form one recognition restriction endonuclease cut site for an EcoRI recognition restriction endonuclease and one recognition restriction endonuclease cut site for an XbaI recognition restriction endonuclease upon target nucleic acid hybridization. In such cases, each recognition restriction endonuclease can be used individually or in combination (e.g., as a mixture) to cleave probe nucleic acid that hybridized to target nucleic acid and formed the corresponding recognition restriction endonuclease cut site via such hybridization.

Probe nucleic acid can be designed such that any target nucleic acid can be detected. Examples of target nucleic acid that can be detected using the methods and materials provided herein include, without limitation, human nucleic acid, microbial nucleic acid (e.g., bacterial, fungal, or protozoan nucleic acid), viral nucleic acid, nucleic acid containing a point mutation, SNP, or gene rearrangement, mammalian nucleic acid, methylated nucleic acid, and mRNA. When detecting RNA target nucleic acid, restriction endonucleases having the ability to cleave a recognition restriction endonuclease cut site that is created between a DNA section of the probe nucleic acid and the RNA target nucleic acid can be used as recognition restriction endonucleases. Examples of such restriction endonucleases include, without limitation, HhaI, AluI, TaqI, HaeIII, EcoRI, HindII, SalI, and MspI restriction endonucleases. When detecting methylated target nucleic acid (e.g., a methylated target nucleic acid associated with cancer), restriction endonucleases having the ability to cleave a recognition restriction endonuclease cut site that includes a methylated nucleotide to be assessed can be used as recognition restriction endonucleases. Examples of restriction endonucleases having the ability to recognize methylated nucleotides include, without limitation, DpnI, GlaI, HpaII, MspI, AciI, HhaI, and SssI restriction endonucleases. In such cases, a control can include detecting the same target nucleic acid without the methylated nucleotide. In some cases, a combination of methylation insensitive and methylation sensitive restriction endonucleases can be used to assess a sample for methylated target nucleic acid. For example, similar generation of cleavage products using both methylation insensitive and methylation sensitive restriction endonucleases designed for the same site can indicate that the target nucleic acid lacks methylation at that site, while an increased level of cleavage products using a methylation insensitive restriction endonuclease as compared to the level generated using a methylation sensitive restriction endonuclease designed for the same site can indicate that the target nucleic acid is methylated at that site.

The nucleotide sequence of target nucleic acid to be detected can be obtained from, for example, common nucleic acid databases such as GenBank®. A portion of target nucleic acid sequence can be selected using a computer-based program. For example, a computer-based program can be used to detect restriction endonuclease cut sites within a portion of target nucleic acid. Such information can be used to design probe nucleic acid such that the single-stranded section creates at least one recognition restriction endonuclease cut site upon hybridization of the target nucleic acid.

Any appropriate method can be used to obtain the nucleic acid component of the probe nucleic acid. For example, common molecular cloning and chemical nucleic acid synthesis techniques can be used to obtain the nucleic acid component of the probe nucleic acid. In some cases, the nucleic acid component of the probe nucleic acid can be synthesized using commercially available automated oligonucleotide synthesizers such as those available from Applied Biosystems (Foster City, Calif.). In some cases, probe nucleic acids can be synthesized de novo using any of a number of procedures widely available in the art. Examples of such methods of synthesis include, without limitation, the β-cyanoethyl phosphoramidite method (Beaucage et al., *Tet. Let.*, 22:1859-1862 (1981)) and the nucleoside H-phosphonate method (Garegg et al., *Tet. Let.*, 27:4051-4054 (1986); Froehler et al., *Nucl. Acid Res.*, 14:5399-5407 (1986); Garegg et al., *Tet. Let.*, 27:4055-4058 (1986); and Gaffney et al., *Tet. Let.*, 29:2619-2622 (1988)). These methods can be performed by a variety of commercially-available automated oligonucleotide synthesizers. In some cases, recombinant nucleic acid techniques such as PCR and those that include using restriction enzyme digestion and ligation of existing nucleic acid sequences (e.g., genomic DNA or cDNA) can be used to obtain the nucleic acid component of the probe nucleic acid.

Probe nucleic acid described herein can be attached to a solid support. Examples of solid supports include, without limitation, a well of a microtiter plate (e.g., a 96-well microtiter plate or ELISA plate), beads (e.g., magnetic, glass, plastic, or gold-coated beads), slides (e.g., glass or gold-coated slides), micro- or nano-particles (e.g., carbon nanotubes), platinum solid supports, palladium solid supports, and a surface of a chamber or channel within a microfluidic device. In some cases, a solid support can be a silicon oxide-based solid support, a plastic polymer-based solid support (e.g., a nylon, nitrocellulose, or polyvinylidene fluoride-based solid support), or a biopolymer-based (e.g., a cross-linked dextran or cellulose-based solid support) solid support. Probe nucleic acid can be directly or indirectly attached to a solid support. For example, biotin can be a component of the probe nucleic acid, and the probe nucleic acid containing biotin can be indirectly attached to a solid support that is coated with streptavidin via a biotin-streptavidin interaction. In some cases, probe nucleic acid can be attached to a solid support via a covalent or non-covalent interaction. For example, probe nucleic acid can be covalently attached to magnetic beads as described elsewhere (Albretsen et al., *Anal. Biochem.*, 189(1):40-50 (1990)).

Probe nucleic acid can be designed to contain any type of restriction endonuclease as an amplifying restriction endonuclease. In general, an amplifying restriction endonuclease of the probe nucleic acid is typically a different restriction endonuclease than the restriction endonuclease that is used as a recognition restriction endonuclease. For example, when an EcoRI restriction endonuclease is used as a recognition restriction endonuclease, a restriction endonuclease other than an EcoRI restriction endonuclease (e.g., a HindIII restriction endonuclease) is used as an amplifying restriction endonuclease. Examples of restriction endonucleases that can be used as amplifying restriction endonucleases include, without limitation, EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SphI, StuI, XbaI, AarI, BanII, BseGI, BspPI, CfrI, EcoNI, Hsp92II, NlaIV, RsaI, TaiI, AasI, BbsI, BseJI, BspTI, ClaI, EcoO109I, I-PpoI, NmuCI, RsrII, TaqaI, AatII, BbuI, BseLI, BsrBI, CpoI, KasI, Acc65I, BbvCI, BseMI, BsrDI, Csp45I, Kpn2I, NruI, SacII, TasI, AccB7I, BbvI, BseMII, BsrFI, Csp6I, EheI, KpnI, NsbI, SalI, TatI, AccI, BceAI, BseNI, BsrGI, CspI, Esp3I, KspAI, NsiI, SapI, and TauI restriction endonucleases. Any number of molecules of the same amplifying restriction endonuclease can be attached to one probe nucleic acid molecule. For example, a single probe nucleic acid molecule can contain one, two, three, four, five, or more EcoRI amplifying restriction endonuclease molecules. In some cases, a single probe nucleic acid molecule can contain two or more (e.g., two, three, four, five, or more) different types of amplifying restriction endonucleases. For example, a single probe nucleic acid molecule can contain three EcoRI amplifying restriction endonuclease molecules and two BanII amplifying restriction endonuclease molecules.

Any appropriate method can be used to attach an amplifying restriction endonuclease to a nucleic acid component of the probe nucleic acid. In some cases, an amplifying restriction endonuclease can be attached by an ionic or covalent attachment. For example, covalent bonds such as amide bonds, disulfide bonds, and thioether bonds, or bonds formed by crosslinking agents can be used. In some cases, a non-covalent linkage can be used. The attachment can be a direct attachment or an indirect attachment. For example, a linker can be used to attach an amplifying restriction endonuclease to a nucleic acid component of the probe nucleic acid. In some cases, nucleic acid can include a thiol modification, and a restriction endonuclease can be conjugated to the thiol-containing nucleic acid based on succinimidyl 4-[N-maleimidomethyl]cyclohexane-1-carboxylate (SMCC) using techniques similar to those described elsewhere (Dill et al., *Biosensors and Bioelectronics*, 20:736-742 (2004)). In some cases, a biotinylated nucleic acid and a streptavidin-containing restriction endonuclease can be attached to one another via a biotin-streptavidin interaction. A restriction endonuclease can be conjugated with streptavidin using, for example, sulfosuccinimidyl 6-(3'-[2-pyridyldithio]-propionamido)hexanoate. An amplifying restriction endonuclease can be attached at any location of a nucleic acid component of the probe nucleic acid. For example, an amplifying restriction endonuclease can be attached at an end (e.g., a 5' end or 3' end) of a nucleic acid component, in the middle of a nucleic acid component, or at any position along the length of a nucleic acid component.

Signal expansion nucleic acid (e.g., first signal expansion nucleic acid and second signal expansion nucleic acid) and reporter nucleic acid described herein typically include at least one double-stranded DNA section that includes an amplifying restriction endonuclease cut site (e.g., an initial amplifying restriction endonuclease cut site, a secondary amplifying restriction endonuclease cut site, or a tertiary amplifying restriction endonuclease cut site). The other portions of the signal expansion nucleic acid or reporter nucleic acid can include DNA, RNA, or other molecules. For example, reporter nucleic acid can include biotin such that the reporter nucleic acid can be attached to a streptavidin-coated solid support. In some cases, one or both strands of the double-stranded section of the signal expansion nucleic acid or the reporter nucleic acid that contains an amplifying restriction endonuclease cut site can be RNA or a nucleic acid analog (e.g., a peptide nucleic acid (PNA)) provided that such a double-stranded section is capable of being cleaved by the amplifying restriction endonuclease. Examples of restriction endonucleases that can be used as amplifying restriction endonucleases to cleave a DNA:RNA hybrid section of signal expansion nucleic acid or reporter nucleic acid include, without limitation, HhaI, AluI, TaqI, HaeIII, EcoRI, HindII, SalI, and MspI restriction endonucleases.

Signal expansion nucleic acid or reporter nucleic acid described herein can be any length provided that the double-stranded section that contains the amplifying restriction endonuclease cut site is capable of being cleaved by the amplifying restriction endonuclease. In general, the double-stranded section of signal expansion nucleic acid or reporter nucleic acid can be between about 10 and about 500 or more nucleotides (e.g., between about 10 and about 400 nucleotides, between about 10 and about 300 nucleotides, between about 10 and about 200 nucleotides, between about 10 and about 100 nucleotides, between about 10 and about 50 nucleotides, between about 10 and about 25 nucleotides, between about 20 and about 500 nucleotides, between about 30 and about 500 nucleotides, between about 40 and about 500 nucleotides, between about 50 and about 500 nucleotides, between about 15 and about 50 nucleotides, between about 15 and about 25 nucleotides, between about 20 and about 50 nucleotides, or between about 18 and about 25 nucleotides) in length. In some cases, the double-stranded section of signal expansion nucleic acid or reporter nucleic acid can be between 5 and 50 nucleotides in length. The amplifying restriction endonuclease cut site of the signal expansion nucleic acid or the reporter nucleic acid can be located at any position alone the double-stranded section. For example, the amplifying restriction endonuclease cut site can be towards the 5' end, towards the '3 end, or near the center of the double-stranded section of the signal expansion nucleic acid or the reporter nucleic acid. In general, the overall length of signal expansion nucleic acid or reporter nucleic acid described herein can be between about 10 and about 2500 or more nucleotides (e.g., between about 10 and about 2000 nucleotides, between about 10 and about 1000 nucleotides, between about 10 and about 500 nucleotides, between about 10 and about 400 nucleotides, between about 10 and about 300 nucleotides, between about 10 and about 200 nucleotides, between about 10 and about 100 nucleotides, between about 10 and about 50 nucleotides, between about 10 and about 25 nucleotides, between about 20 and about 500 nucleotides, between about 30 and about 500 nucleotides, between about 40 and about 500 nucleotides, between about 50 and about 500 nucleotides, between about 75 and about 500 nucleotides, between about 100 and about 500 nucleotides, between about 150 and about 500 nucleotides, between about 15 and about 50 nucleotides, between about 15 and about 25 nucleotides, between about 20 and about 50 nucleotides, or between about 18 and about 25 nucleotides) in length.

The amplifying restriction endonuclease cut site of signal expansion nucleic acid or reporter nucleic acid described herein can be a cut site of any type of restriction endonuclease. In addition, any type of restriction endonuclease can be used as an amplifying restriction endonuclease to cleave signal expansion nucleic acid or reporter nucleic acid. Examples of restriction endonucleases that can be used as amplifying restriction endonucleases include, without limitation, EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SphI, StuI, XbaI, AarI, BanII, BseGI, BspPI, CfrI, EcoNI, Hsp92II, NlaIV, RsaI, TaiI, AasI, BbsI, BseJI, BspTI, ClaI, EcoO109I, I-PpoI, NmuCI, RsrII, TaqaI, AatII, BbuI, BseLI, BsrBI, CpoI, KasI, Acc65I, BbvCI, BseMI, BsrDI, Csp45I, Kpn2I, NruI, SacII, TasI, AccB7I, BbvI, BseMII, BsrFI, Csp6I, EheI, KpnI, NsbI, SalI, TatI, AccI, BceAI, BseNI, BsrGI, CspI, Esp3I, KspAI, NsiI, SapI, and TauI restriction endonucleases.

In general, signal expansion nucleic acid or reporter nucleic acid can be designed to have a double-stranded section that contains a single amplifying restriction endonuclease cut site. In some cases, signal expansion nucleic acid or reporter nucleic acid provided herein can be designed to have a double-stranded section that contains more than one (e.g., two, three, four, five, six, seven, eight, nine, ten, or more) amplifying restriction endonuclease cut site. When more than one amplifying restriction endonuclease cut site is used, the multiple amplifying restriction endonuclease cut sites can be cut sites for the same restriction endonuclease or cut sites for different restriction endonucleases. For example, reporter nucleic acid can be designed to have a double-stranded section that contains one initial amplifying restriction endonuclease cut site for an EcoRI initial amplifying restriction endonuclease and one secondary amplifying restriction endonuclease cut site for an XbaI secondary amplifying restriction endonuclease.

Any appropriate method can be used to obtain the nucleic acid component of signal expansion nucleic acid or reporter nucleic acid. For example, common molecular cloning and chemical nucleic acid synthesis techniques can be used to obtain the nucleic acid component of signal expansion nucleic acid or reporter nucleic acid. In some cases, the nucleic acid component of signal expansion nucleic acid or reporter nucleic acid can be synthesized using commercially available automated oligonucleotide synthesizers such as those available from Applied Biosystems (Foster City, Calif.). In some cases, signal expansion nucleic acid or reporter nucleic acid can be synthesized de novo using any of a number of procedures widely available in the art. Examples of such methods of synthesis include, without limitation, the β-cyanoethyl phosphoramidite method (Beaucage et al., *Tet. Let.*, 22:1859-1862 (1981)) and the nucleoside H-phosphonate method (Garegg et al., *Tet. Let.*, 27:4051-4054 (1986); Froehler et al., *Nucl. Acid Res.*, 14:5399-5407 (1986); Garegg et al., *Tet. Let.*, 27:4055-4058 (1986); and Gaffney et al., *Tet. Let.*, 29:2619-2622 (1988)). These methods can be performed by a variety of commercially-available automated oligonucleotide synthesizers. In some cases, recombinant nucleic acid techniques such as PCR and those that include using restriction enzyme digestion and ligation of existing nucleic acid sequences (e.g., genomic DNA or cDNA) can be used to obtain the nucleic acid component of signal expansion nucleic acid or reporter nucleic acid.

Signal expansion nucleic acid or reporter nucleic acid described herein can be attached to a solid support. Examples of solid supports include, without limitation, a well of a microtiter plate (e.g., a 96-well microtiter plate or ELISA plate), beads (e.g., magnetic, glass, plastic, or gold-coated beads), slides (e.g., glass or gold-coated slides), micro- or nano-particles (e.g., carbon nanotubes), platinum solid supports, palladium solid supports, and a surface of a chamber or channel within a microfluidic device. In some cases, a solid support can be a silicon oxide-based solid support, a plastic polymer-based solid support (e.g., a nylon, nitrocellulose, or polyvinylidene fluoride-based solid support) or a biopolymer-based (e.g., a cross-linked dextran or cellulose-based solid support) solid support.

Signal expansion nucleic acid or reporter nucleic acid can be directly or indirectly attached to a solid support. For example, biotin can be a component of signal expansion nucleic acid or reporter nucleic acid, and the signal expansion nucleic acid or the reporter nucleic acid containing biotin can be indirectly attached to a solid support that is coated with streptavidin via a biotin-streptavidin interaction. In some cases, signal expansion nucleic acid or reporter nucleic acid can be attached to a solid support via a covalent or non-covalent interaction. For example, signal expansion nucleic acid or reporter nucleic acid can be covalently attached to magnetic beads as described elsewhere (Albretsen et al., *Anal. Biochem.*, 189(1):40-50 (1990)).

Signal expansion nucleic acid can be designed to contain any type of restriction endonuclease as an amplifying restriction endonuclease (e.g., an initial amplifying restriction endonuclease, a secondary amplifying restriction endonuclease, or a tertiary amplifying restriction endonuclease). In general, an amplifying restriction endonuclease of signal expansion nucleic acid is typically a different restriction endonuclease than the restriction endonuclease that is used as a recognition restriction endonuclease. For example, when an EcoRI restriction endonuclease is used as a recognition restriction endonuclease, a restriction endonuclease other than an EcoRI restriction endonuclease (e.g., a HeaIII restriction endonuclease) is used as an amplifying restriction endonuclease. Examples of restriction endonucleases that can be used as amplifying restriction endonucleases include, without limitation, EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SphI, StuI, XbaI, AarI, BanII, BseGI, BspPI, CfrI, EcoNI, Hsp92II, NlaIV, RsaI, TaiI, AasI, BbsI, BseJI, BspTI, ClaI, EcoO109I, I-PpoI, NmuCI, RsrII, TaqaI, AatII, BbuI, BseLI, BsrBI, CpoI, KasI, Acc65I, BbvCI, BseMI, BsrDI, Csp45I, Kpn2I, NruI, SacII, TasI, AccB7I, BbvI, BseMII, BsrFI, Csp6I, EheI, KpnI, NsbI, SalI, TatI, AccI, BceAI, BseNI, BsrGI, CspI, Esp3I, KspAI, NsiI, SapI, and TauI restriction endonucleases. Any number of molecules of the same amplifying restriction endonuclease can be attached to one signal expansion nucleic acid molecule. For example, a single signal expansion nucleic acid molecule can contain one, two, three, four, five, or more EcoRI amplifying restriction endonuclease molecules. In some cases, a single signal expansion nucleic acid molecule can contain two or more (e.g., two, three, four, five, or more) different types of amplifying restriction endonucleases. For example, a single signal expansion nucleic acid molecule can contain three BanII amplifying restriction endonuclease molecules and two SacII amplifying restriction endonuclease molecules.

Reporter nucleic acid can be designed to contain a label to aid in the detection of cleaved reporter nucleic acid. In some cases, signal expansion nucleic acid can be designed to contain a label. In such cases, signal expansion nucleic acid containing a label can be used in addition to reporter nucleic acid or in place of reporter nucleic acid to detect target nucleic acid. Examples of labels that can be a component of reporter nucleic acid or signal expansion nucleic acid include, without limitation, fluorescent labels (with or without the use of quenchers), dyes, antibodies, radioactive material, enzymes (e.g., horse radish peroxidase, alkaline phosphatese, laccase, galactosidase, or luciferase), redox labels (e.g., ferrocene redox labels), metallic particles (e.g., gold nanoparticles), green fluorescent protein-based labels. In some cases, for a redox label, such as ferrocene, the detector can be an electrode for amperometric assay of redox molecules. For example, if the redox label is present in a reduced form of ferrocene, then the electrode at high electrode potential can provide an oxidation of the reduced form of ferrocene, thereby converting it to an oxidized form of ferrocene. The generated current can be proportional to the concentration of ferrocene label in the solution.

In one embodiment, reporter nucleic acid or signal expansion nucleic acid can contain a fluorescent label and a quencher such that cleaved reporter nucleic acid provides a fluorescent signal and uncleaved reporter nucleic acid does not provide a fluorescent signal. In some cases, the reporter nucleic acid or signal expansion nucleic acid can contain a label (e.g., a fluorescent label or an enzyme such as horse radish peroxidase) and can be attached to a solid support (e.g., a well of a microtiter plate). For example, the reporter nucleic acid or signal expansion nucleic acid can be attached to a solid support such that cleavage at the amplifying restriction endonuclease cut site by the amplifying restriction endonuclease releases a portion of the reporter nucleic acid or the signal expansion nucleic acid that contains the label. The resulting reaction mixture can be collected and assessed for the presence, absence, or amount of released portions of the reporter nucleic acid or signal expansion nucleic acid using the label. For example, the released portions of the reporter nucleic acid or the signal expansion nucleic acid, if present, can be transferred from one well of a microtiter plate (e.g., a 96-well plate) that contained the reporter nucleic acid or the signal expansion nucleic acid to another well of a microtiter plate, where the transferred material can be assessed for a signal from the label. Any number of molecules of a label can be attached to one reporter nucleic acid molecule or one signal expansion nucleic acid molecule. For example, a reporter nucleic acid molecule or a single signal expansion nucleic acid molecule can contain one, two, three, four, five, or more fluorescent molecules.

Any appropriate method can be used to attach a label to a nucleic acid component of reporter nucleic acid or signal expansion nucleic acid. In some cases, a label can be attached by an ionic or covalent attachment. For example, covalent bonds such as amide bonds, disulfide bonds, and thioether bonds, or bonds formed by crosslinking agents can be used. In some cases, a non-covalent linkage can be used. The attachment can be a direct attachment or an indirect attachment. For example, a linker can be used to attach a label to a nucleic acid component of reporter nucleic acid or signal expansion nucleic acid. In some cases, nucleic acid can include a thiol modification, and a label can be conjugated to the thiol-containing nucleic acid based on succinimidyl 4-[N-maleimidomethyl]cyclo-hexane-1-carboxylate (SMCC) using techniques similar to those described elsewhere (Dill et al., Biosensors and Bioelectronics, 20:736-742 (2004)). In some cases, a biotinylated nucleic acid and a streptavidin-containing label can be attached to one another via a biotin-streptavidin interaction. A label can be conjugated with streptavidin using, for example, sulfosuccinimidyl 6-(3'-[2-pyridyldithio]-propionamido)hexanoate. A label can be attached at any location of a nucleic acid component of reporter nucleic acid or signal expansion nucleic acid. For example, a label can be attached at an end (e.g., a 5' end or 3' end) of a nucleic acid component, in the middle of a nucleic acid component, or at any position along the length of a nucleic acid component of reporter nucleic acid or signal expansion nucleic acid.

The methods and materials provided herein can be used to detect target nucleic acid in any type of sample. For example, blood samples, serum samples, saliva samples, nasal swab samples, stool samples, urine samples, tissue samples (e.g., tissue biopsy samples), environmental samples (e.g., water samples, soil samples, and air samples), food samples (e.g., meat samples, produce samples, or drink samples), and industrial samples (e.g., air filter samples and samples collected from work stations) can be collected and assessed for target nucleic acid. Once obtained, a sample to be assessed can be processed to obtain nucleic acid. For example, a nucleic acid extraction can be performed on a tissue sample to obtain a sample that is enriched for nucleic acid. In some cases, a sample can be heated or treated with a cell lysis agent to release nucleic acid from cells present in the sample.

Once obtained, a sample to be assessed can be contacted with a probe nucleic acid as described herein. This contacting step can be carried out for any period of time and at any temperature that allows target nucleic acid to hybridize with probe nucleic acid. For example, this step can be performed between 10 seconds and 24 hours (e.g., between 30 seconds and 12 hours, between 30 seconds and 8 hours, between 30 seconds and 4 hours, between 30 seconds and 2 hours, between 30 seconds and 1 hour, between 1 minute and 24 hours, between 1 minute and 12 hours, between 1 minute and 8 hours, between 1 minute and 4 hours, between 1 minute and 2 hours, between 1 minute and 1 hour, between 5 minutes and 1 hour, between 10 minutes and 1 hour, between 15 minutes and 1 hour, or between 30 minutes and 1 hour). The initial temperature can be between 15° C. and 100° C. (e.g., between 23° C. and 98° C., between 23° C. and 90° C., between 23° C. and 85° C., between 23° C. and 75° C., between 23° C. and 65° C., between 23° C. and 55° C., between 23° C. and 45° C., between 23° C. and 35° C., between 30° C. and 95° C., between 30° C. and 85° C., between 30° C. and 75° C., between 30° C. and 65° C., between 30° C. and 55° C., between 30° C. and 45° C., between 20° C. and 40° C., between 20° C. and 30° C., and between 25° C. and 35° C.). The temperature during this contacting step can remain constant or can be increased or decreased. For example, the initial temperature can be between about 40° C. and about 85° C., and then the temperature can be allowed to decrease to room temperature over a period of about 30 seconds to about 30 minutes (e.g., between about 30 seconds and about 15 minutes, between about 30 seconds and about 10 minutes, between about 1 minute and about 30 minutes, between about 1 minute and about 15 minutes, or between about 1 minute and about 5 minutes).

Contact of the sample (e.g., a sample to be tested or suspected to contain target nucleic acid) with probe nucleic acid can occur in the presence of the recognition restriction endonucleases, or a separate step of adding the recognition restriction endonucleases to the reaction can be performed. The recognition restriction endonuclease step can be carried out for any period of time and at any temperature that allows the recognition restriction endonuclease to cleave recognition restriction endonuclease cut sites formed by the hybridization of target nucleic acid to the probe nucleic acid. For example, this step can be performed between one second and 24 hours (e.g., between one second and 30 minutes, between one second and one hour, between five seconds and one hour, between 30 seconds and 24 hours, between 30 seconds and 12 hours, between 30 seconds and 8 hours, between 30 seconds and 4 hours, between 30 seconds and 2 hours, between 30 seconds and 1 hour, between 1 minute and 24 hours, between 1 minute and 12 hours, between 1 minute and 8 hours, between 1 minute and 4 hours, between 1 minute and 2 hours, between 1 minute and 1 hour, between 5 minutes and 1 hour, between 10 minutes and 1 hour, between 15 minutes and 1 hour, or between 30 minutes and 1 hour). The temperature can be between 15° C. and 75° C. (e.g., between 15° C. and 75° C., between 15° C. and 65° C., between 15° C. and 55° C., between 15° C. and 45° C., between 15° C. and 35° C., between 15° C. and 30° C., between 23° C. and 55° C., between 23° C. and 45° C., between 30° C. and 65° C., between 30° C. and 55° C., between 30° C. and 45° C., between 30° C. and 40° C., between 35° C. and 40° C., and between 36° C. and 38° C.). Any appropriate concentration of recognition restriction endonuclease can be used. For example, between about 0.001 units and 1000 units (e.g., between about 0.001 units and 750 units, between about 0.001 units and 500 units, between about 0.001 units and 250 units, between about 0.001 units and 200 units, between about 0.001 units and 150 units, between about 0.001 units and 100 units, between about 0.001 units and 50 units, between about 0.001 units and 25 units, between about 0.001 units and 10 units, between about 0.001 units and 1 unit, between about 0.001 units and 0.1 units, between about 0.01 units and 1000 units, between about 0.1 units and 1000 units, between about 1 unit and 1000 units, between about 10 units and 1000 units, between about 50 units and 1000 units, between about 0.5 units and 100 units, or between about 1 unit and 100 units) of restriction endonuclease can be used. Other restriction endonuclease reaction conditions such as salt conditions can be used according to manufacture's instructions.

When one step of a method provided herein is completed, the resulting reaction product containing cleaved nucleic acid can be used in the next step. For example, cleaved nucleic acid of a reaction product can be removed from uncleaved nucleic acid and used in the next step of the method. For example, when probe nucleic acid is attached to a solid support, the released portions of probe nucleic acid that contain an amplifying restriction endonuclease can be collected and placed in contact with reporter nucleic acid or signal expansion nucleic acid as described herein. The resulting reaction products of a particular step can be manually or automatically (e.g., robotically) transferred to a location containing nucleic acid for the next step (e.g., reporter nucleic acid or signal expansion nucleic acid), which nucleic acid can be attached or not attached to a solid support. In some cases, one reaction of a method described herein can be carried out at one location (e.g., a chamber) of a microfluidic device or blister package device, and the reaction products that are generated can be moved to another location (e.g., another chamber) that contains nucleic acid for the next step (e.g., reporter nucleic acid or signal expansion nucleic acid) via a channel. In some cases, cleaved nucleic acid of a reaction product can be used in the next step of the method by removing the uncleaved nucleic acid from the reaction product. For example, when magnetic beads are used as a solid support, a magnetic force can be used to remove the magnetic beads and any attached uncleaved nucleic acid from the reaction product.

Any appropriate method can be used to detect cleaved reporter nucleic acid and/or signal expansion nucleic acid to determine the presence, absence, or amount of target nucleic acid in a sample. For example, size separation techniques can be used to assess reaction products for cleaved reporter nucleic acid and/or signal expansion nucleic acid. Examples of such size separation techniques include, without limitation, gel electrophoresis and capillary electrophoresis techniques. In some cases, a melt curve analysis can be performed to assess reaction products for cleaved reporter nucleic acid and/or signal expansion nucleic acid. As described herein, a label can be used to aid in the detection of cleaved nucleic acid (e.g., reporter nucleic acid and/or signal expansion nucleic acid). Examples of labels that can be used include, without limitation, fluorescent labels (with or without the use of quenchers), dyes, antibodies, radioactive material, enzymes (e.g., horse radish peroxidase, alkaline phosphatese, laccase, galactosidase, or luciferase), redox labels (e.g., ferrocene redox labels), metallic particles (e.g., gold nanoparticles), and green fluorescent protein based labels. For example, the release of fluorescently labeled portions of reporter nucleic acid and/or signal expansion nucleic acid from a solid support can be assessed using common fluorescent label detectors. In some cases, cleaved reporter nucleic acid and/or signal expansion nucleic acid can be detected electrochemically. For electrochemical detection, the reporter nucleic acid and/or signal expansion nucleic acid can include a ferrocene redox label. Reporter nucleic acid and/or signal expansion nucleic acid containing ferrocene can be obtained by coupling ferrocene carboxylic acid with an amino-modified oligonucleotide using the carbodiimide reaction in the presence of an excess of ferrocene carboxylic acid. In one embodiment, for a redox label, such as ferrocene, the detector can be an electrode for amperometric assay of redox molecules. For example, if the redox label is present in a reduced form of ferrocene, then the electrode at high electrode potential can provide an oxidation of the reduced form of ferrocene, thereby converting it to an oxidized form of ferrocene. The generated current can be proportional to the concentration of ferrocene label in the solution.

The methods and materials provided herein can be used to assess one or more samples for target nucleic acid in real-time. For example, a fluorescent label/quencher system or an electrochemical redox label system can be used to detect cleavage of reporter nucleic acid and/or signal expansion nucleic acid in real time.

The methods and materials provided herein can be used to assess one or more samples (e.g., two, three, four, five, six, seven, eight, nine, ten, 20, 50, 100, 500, 1000, or more) for a single type of target nucleic acid. In some case, the methods and materials provided herein can be used in a multiplex manner to assess one or more samples for more than one (e.g., two, three, four, five, six, seven, eight, nine, ten, 20, 50, 100, 500, 1000, or more) type of target nucleic acid. For example, target nucleic acid for ten different sequences (e.g., ten different sequences from a single bacterial species or strain, or a different sequence from ten different bacterial species or strains) can be used to design ten different probe nucleic acid molecules. In such cases, a different label used to correspond to each probe nucleic acid such that the detected signals can indicate which of the ten target nucleic acids are being detected.

This document also provides kits for performing the methods described herein. For example, a kit provided herein can include probe nucleic acid with or without being attached to a solid support and/or reporter nucleic acid with or without being attached to a solid support. In some cases, such a kit can include a recognition restriction endonuclease, first signal expansion nucleic acid, second signal expansion nucleic acid, or a combination thereof. In some cases, a kit can be configured into a microfluidic device that allows for the movement of probe nucleic acid, first signal expansion nucleic acid, second signal expansion nucleic acid, reporter nucleic acid, or recognition restriction endonucleases (or any combination thereof) as well as a cleaved portion of any such nucleic acid in a manner that allows a detection method provided herein to be carried out with or without the nucleic acid being attached to a solid support. For example, a kit provided herein can be a microfluidic device capable of receiving a sample and contacting that sample with probe nucleic acid. The probe nucleic acid can be designed to include a length of nucleotides followed by the sequence complementary to the target nucleic acid, which can create a recognition restriction endonuclease cut site, followed by an amplifying restriction endonuclease. The distance from the recognition restriction endonuclease cut site to the amplifying restriction endonuclease can be relatively short (e.g., 100, 50, 25, 10, or less nucleotides), while the distance from the recognition restriction endonuclease cut site to the beginning of the length of nucleotides can be relatively long (e.g., 50, 100, 150, 200, 500, 1000, 2000, or more). In such cases, cleavage of the probe nucleic acid at the recognition restriction endonuclease cut site can result in a relatively small portion that contains the amplifying restriction endonuclease and is capable of travelling faster than the larger uncleaved probe nucleic acid. This difference can allow the cleaved portion containing the amplifying restriction endonuclease to reach an area of the microfluidic device containing signal expansion nucleic acid or reporter nucleic acid so that the next reaction can be carried out without the presence of uncleaved probe nucleic acid. In some cases, after the smaller portion containing the amplifying restriction endonuclease enters the area containing signal expansion nucleic acid or reporter nucleic acid, a valve can be used to prevent the larger uncleaved probe nucleic acid from entering. In some cases, a filter can be used to limit the ability of larger uncleaved probe nucleic acid from proceeding to the next reaction location. Similar approaches can be used during other steps of a method provided herein to separate cleaved nucleic acid from uncleaved nucleic acid.

In some cases, a kit provided herein can be a portable or self-contained device, packet, vessel, or container that can be used, for example, in field applications. For example, such a kit can be configured to allow a user to insert a sample for analysis. Once inserted, the sample can be heated (e.g., heated to about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, or more ° C.) and/or cooled by a heating or cooling mechanism located within the kit. For example, an exothermic or endothermic chemical reaction can be initiated within the kit to increase, decrease, or maintain the temperature. Such exothermic or endothermic chemical reactions can be carried out within the kit without being in fluid communication with the reactions of the target nucleic acid detection method. An iron oxidation reaction is an example of an exothermic chemical reaction that can be used to heat a kit provided herein. An endothermic chemical reaction that can be used to cool a kit provided herein can be a reaction that includes the use of ammonium chloride and water, potassium chloride and water, or sodium carbonate and ethanoic acid. In general, when detecting DNA target nucleic acid, the kit can be designed to generate, if needed, enough heat to denature double stranded DNA present within the sample. The kit also can be designed to generate appropriate heating and cooling temperatures to carry out each step of a detection method provided herein. In some cases, a kit provided herein can include a temperature indicator (e.g., color indicator or thermometer) to allows a user to assess temperature.

In some cases, a kit can be designed to provide a user with a "yes" or "no" indication about the presence of target nucleic acid within a tested sample. For example, a label having the ability to generate a change in pH can be used, and a visual indicator (e.g., a pH-based color indicator) can be used to inform the user of the presence of target nucleic acid based on a change in pH.

The invention will be further described in the following examples, which do not limit the scope of the invention described in the claims.

EXAMPLES

Example 1—Formation and Cleavage of Target-Probe Hybrids

An oligonucleotide probe (5'-thiol-GGT AGT GCG AAA TGC CAT TGC TAG TTG TTT-biotin-3'; SEQ ID NO:1) that was modified with a thiol group at the 5' end and a biotin molecule at the 3' end was conjugated to horseradish peroxidase (HRP). Conjugation was performed using the SMCC reagent according to a technique modified from Dill et al. (*Biosensors and Bioelectronics*, 20:736-742 (2004)). The HRP conjugate solution was incubated with a streptavidin-coated ELISA plate to immobilize the HRP-oligonucleotide probe to the surface via a biotin-streptavidin interaction. The ELISA plate was then incubated with different concentrations of a target oligonucleotide (5'-AAA CAA CTA GCA ATG GCA TTT-3'; SEQ ID NO:2). The target oligonucleotide sequence was reverse-complementary to the probe sequence to form a double-stranded hybrid molecule. After washing, the plate was incubated in a solution containing the restriction endonuclease BfaI. BfaI specifically recognizes the sequence 5'-CTAG-3' and cleaves the double-stranded, target-probe hybrids to release the HRP-oligonucleotide into the reaction solution. After a two-hour incubation at 37° C., the reaction solution was transferred to a new ELISA plate. The cleaved HRP-oligonucleotide was contacted to 3,3', 5,5'-tetramethyl benzidine (TMB) to form a colored reaction product.

Figure 6:
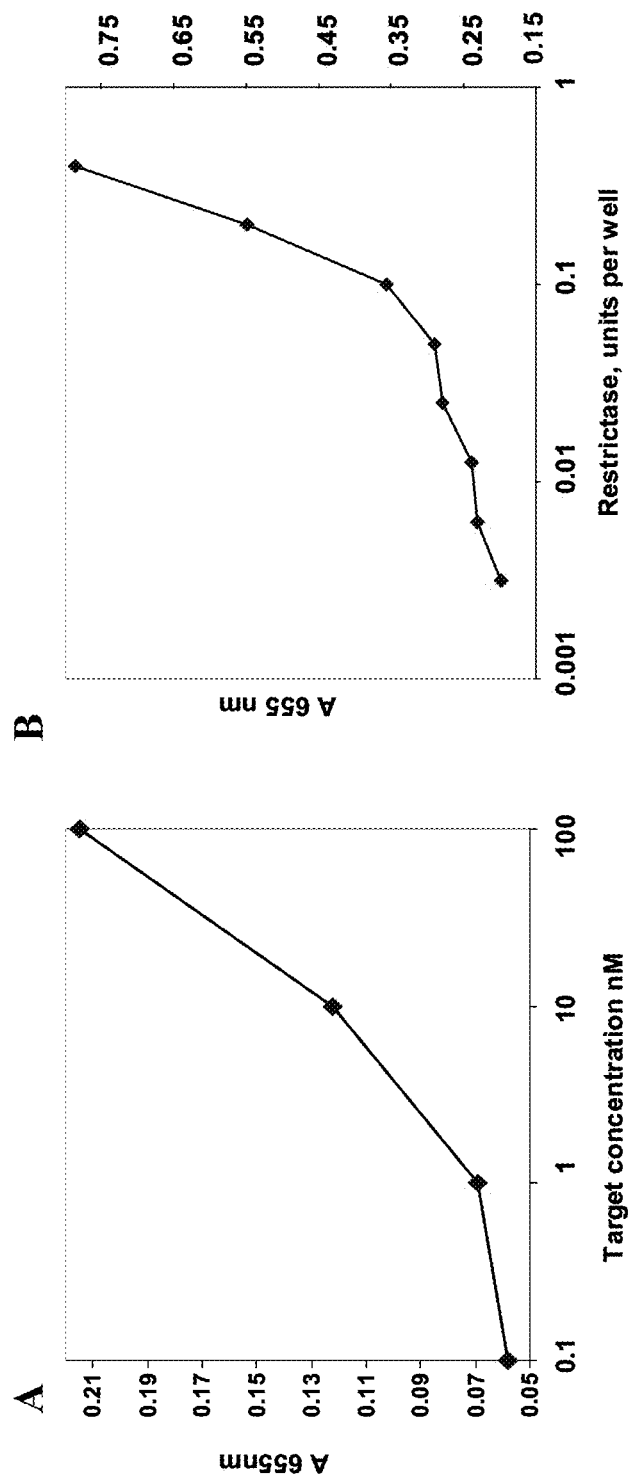
FIG. 6 contains line graphs demonstrating the effect of target oligonucleotide concentration (A) and recognition restriction endonuclease concentration (B) on the cleavage of HRP-labeled nucleic acid as detected by the formation of colored reaction product.

When the restriction endonuclease BfaI was added in excess to the reaction mixture, a clear direct dependence between the amount of released HRP-probe and the concentration of oligonucleotide target was observed (FIG. 6A). The detectable target concentration was approximately 1 nM. This detection limit was obtained by direct measurement without any secondary signal amplification. The addition of a restriction endonuclease signal amplification cascade as described herein can further improve the detection limit by several orders of magnitude.

When the HRP-oligonucleotide probes were pre-incubated with an excess of target oligonucleotide (500 nM), the amount of cleaved HRP-oligonucleotide probe was limited by the amount of recognition restriction endonuclease BfaI (FIG. 6B). Taken together, these data demonstrate that recognition restriction endonucleases can be used to initiate the restriction endonuclease cascades described herein.

Example 2—Detecting Target Nucleic Acid Using Probe Nucleic Acid and Reporter Nucleic Acid A target nucleic acid is selected. Once selected, target nucleic acid is analyzed using a common genetic database such as GenBank® and/or a computer-based sequence analysis program to identify a portion of the target nucleic acid that contains a cut site for a restriction endonuclease. Probe nucleic acid is designed to be complementary to at least a portion of target nucleic acid that contains a cut site. Once designed and obtained by standard oligonucleotide synthesis methods, probe nucleic acid is conjugated to an amplifying restriction endonuclease and immobilized to the surface of a first well of a microtiter plate. A sample to be tested is incubated in the first well. If target nucleic acid is present in the sample, at least a portion of the target nucleic acid hybridizes to the probe nucleic acid, and thereby forms a recognition restriction endonuclease cut site. The recognition restriction endonuclease is added to the first well having the sample and probe nucleic acid. The microtiter plate is incubated at 37° C. for an appropriate length of time for the cleavage reaction to proceed.

Upon cleavage of probe nucleic acid by the recognition restriction endonuclease, the reaction solution containing the released portion of the probe nucleic acid is transferred into a second well. The second well contains reporter nucleic acid that is immobilized to the surface and contains at least one double-stranded portion having an amplifying restriction endonuclease cut site. Reporter nucleic acid also has a fluorescent label. Upon transfer to the second chamber, the amplifying restriction endonuclease bound to the released portion of the probe nucleic acid contacts the reporter nucleic acid. The amplifying restriction endonuclease cleaves reporter nucleic acid at the double-stranded amplifying restriction endonuclease cut site to form at least two portions. The liberated portion of the reporter nucleic acid having the fluorescent label is moved to a third microtiter plate well, and a standard fluorescent reader is used to measure any fluorescent signal.

A standard curve of known amounts of target nucleic acid is used to quantify the amount of target nucleic acid in the tested sample.

Example 3—Detecting Target Nucleic Acid Using Probe Nucleic Acid, First Signal Expansion Nucleic Acid, Second Signal Expansion Nucleic Acid, and Reporter Nucleic Acid Once selected, target nucleic acid is analyzed using a common genetic database such as GenBank® and/or a computer-based sequence analysis program to identify a portion of target nucleic acid that contains a cut site for a restriction endonuclease. Probe nucleic acid is designed based on the desired target nucleic acid as described herein. Standard oligonucleotide synthesis methods are used to make the probe nucleic acid, which is then conjugated to an initial amplifying restriction endonuclease and immobilized to the surface of a first well of a microtiter plate. A sample to be tested for the target nucleic acid is incubated in the first well. If target nucleic acid is present in the sample, at least a portion of target nucleic acid hybridizes to probe nucleic acid and thereby forms a recognition restriction endonuclease cut site. Recognition restriction endonuclease is added to the first well having the sample and probe nucleic acid. The microtiter plate is incubated at 37° C. for an appropriate length of time for the cleavage reaction to proceed. After cleavage of the probe nucleic acid:target nucleic acid hybrid by the recognition restriction endonuclease, the reaction solution containing the free portion of probe nucleic acid is transferred to another well that includes first signal expansion nucleic acid and second signal expansion nucleic acid. The first signal expansion nucleic acid and second signal expansion nucleic acid creates a positive feedback loop that causes an exponential acceleration of release of initial amplifying restriction enzymes. The reaction product from this well is transferred to another well containing reporter nucleic acid, and cleavage of the reporter nucleic acid is used to determine the presence, absence, or amount of target nucleic acid in the sample. A standard curve of known amounts of target nucleic acid is used to quantify the amount of target nucleic acid in the tested sample.

Example 4—Detecting the Presence or Absence of Bacteria

The presence or absence of methicillin-resistant *Staphylococcus aureus* (MRSA) in a sample is detected using an enzymatic amplification cascade. A MRSA-specific target nucleic acid is analyzed using a common genetic database such as GenBank and/or a computer-based sequence analysis program to identify a portion of target nucleic acid that contains a cut site for a restriction endonuclease. Probe nucleic acid is designed to be complementary to at least a portion of the selected target nucleic acid. Once designed and obtained by standard oligonucleotide synthesis methods, probe nucleic acid is conjugated to an amplifying restriction endonuclease and immobilized to the surface of a first well of a microtiter plate. A biological sample (e.g., tissue sample or nasal swab) that is suspected of having MRSA is obtained, and the nucleic acid from that sample is incubated in the first well. If MRSA is present in the sample, at least a portion of the MRSA-specific nucleic acid hybridizes to the probe nucleic acid and thereby forms a recognition restriction endonuclease cut site. Recognition restriction endonuclease is added to the first well having the sample and probe nucleic acid. The microtiter plate is incubated at 37° C. for an appropriate length of time for the cleavage reaction to proceed.

length of time for the cleavage reaction to proceed. The amplifying restriction endonucleases cleave reporter nucleic acid at the double-stranded amplifying restriction endonuclease cut site to form at least two portions. The reaction solution of the second well is transferred to a third well for fluorescence detection using a fluorescent microtiter plate reader. Fluorescence in the third well is indicative of MRSA-specific nucleic acid present in the sample. If the sample was obtained from a patient, such a result is indicative of a MRSA infection in that patient. If no fluorescence is detected in the third well, such a result is indicative of the absence of MRSA in the sample.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: synthetically generated oligonucleotide

<400> SEQUENCE: 1
ggtagtgcga aatgccattg ctagttgttt                                       30

<210> SEQ ID NO 2
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 2
aaacaactag caatggcatt t                                                21
```

After cleavage of the probe nucleic acid:target nucleic acid hybrid by the recognition restriction endonuclease, the reaction solution in the first well is transferred to a second well containing reporter nucleic acid that is immobilized to the surface of the second well and that has at least one double-stranded portion having an amplifying restriction endonuclease cut site. The reporter nucleic acid also has a fluorescent label. In some cases, first signal expansion nucleic acid and second signal expansion nucleic acid are used prior to the report nucleic acid step to increase the level of target nucleic acid detection. The first signal expansion nucleic acid and second signal expansion nucleic acid can include labels in which case they can be used together with reporter nucleic acid or in place of reporter nucleic acid.

After transferring the reaction mixture to the second chamber, the amplifying restriction endonucleases of the released portions of probe nucleic acid contact reporter nucleic acid, and the microtiter plate is incubated at an appropriate temperature (e.g., at 37° C.) for an appropriate

What is claimed is:

1. A method for assessing a sample for target nucleic acid, said method comprising:
   (a) contacting said sample with a probe nucleic acid comprising an amplifying restriction endonuclease and a nucleotide sequence complementary to a sequence of said target nucleic acid under conditions wherein, if said target nucleic acid is present in said sample, at least a portion of said target nucleic acid hybridizes to at least a portion of said probe nucleic acid to form a double-stranded portion of nucleic acid comprising a restriction endonuclease cut site, wherein said probe nucleic acid comprise (i) a single-stranded portion comprising said nucleotide sequence complementary to said sequence of said target nucleic acid and (ii) a double-stranded portion,
   (b) contacting said double-stranded portion of nucleic acid with a recognition restriction endonuclease having the ability to cut said double-stranded portion of nucleic acid at said restriction endonuclease cut site under conditions wherein said recognition restriction endonuclease cleaves said double-stranded portion of nucleic acid at said restriction endonuclease cut site, thereby separating a portion of said probe nucleic acid comprising said amplifying restriction endonuclease from at least another portion of said probe nucleic acid, (c) contacting said portion of said probe nucleic acid comprising said amplifying restriction endonuclease with a reporter nucleic acid comprising a restriction endonuclease, a label, and a double-stranded portion of nucleic acid comprising a restriction endonuclease cut site of said amplifying restriction endonuclease under conditions wherein said amplifying restriction endonuclease cleaves said reporter nucleic acid at said restriction endonuclease cut site of said amplifying restriction endonuclease, thereby separating a portion of said reporter nucleic acid comprising said label from at least another portion of said reporter nucleic acid, and (d) determining the presence or absence of said portion of said reporter nucleic acid using said label, wherein the presence of said portion of said reporter nucleic acid indicates that said sample contains said target nucleic acid, and wherein the absence of said portion of said reporter nucleic acid indicates that said sample does not contain said target nucleic acid.

2. The method of claim 1, wherein said probe nucleic acid is attached to a solid support.

3. The method of claim 2, wherein said portion of said probe nucleic acid comprising said amplifying restriction endonuclease is released from said solid support via said step (b).

4. The method of claim 1, wherein step (a) and step (b) are performed by adding said sample to a compartment comprising said probe nucleic acid and said recognition restriction endonuclease.

5. The method of claim 1, wherein said reporter nucleic acid comprises a first nucleic acid strand comprising said restriction endonuclease and a second nucleic acid strand comprising said label.

6. The method of claim 1, wherein said reporter nucleic acid is attached to a solid support.

7. The method of claim 1, wherein said label is a fluorescent label, a radioactive label, an enzyme label, or a redox label.

8. The method of claim 1, wherein said steps (a), (b), (c), and (d) are performed without nucleic acid amplification.

9. The method of claim 1, wherein said amplifying restriction endonuclease of said probe nucleic acid and said restriction endonuclease of said reporter nucleic acid are the same type of restriction endonuclease.

10. The method of claim 9, wherein said amplifying restriction endonuclease of said probe nucleic acid is HindIII, and wherein said restriction endonuclease of said reporter nucleic acid is HindIII.

11. The method of claim 1, wherein said determining step comprises determining the amount of said target nucleic acid present within said sample.

* * * * *